US011636917B2

(12) United States Patent
Costello et al.

(10) Patent No.: US 11,636,917 B2
(45) Date of Patent: Apr. 25, 2023

(54) SIMULATING THE METABOLIC PATHWAY DYNAMICS OF AN ORGANISM

(71) Applicant: The Regents of the University of California, Oakland, CA (US)

(72) Inventors: Zachary Costello, Berkeley, CA (US); Hector Garcia Martin, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1278 days.

(21) Appl. No.: 16/022,113

(22) Filed: Jun. 28, 2018

(65) Prior Publication Data
US 2019/0005187 A1   Jan. 3, 2019

Related U.S. Application Data

(60) Provisional application No. 62/526,278, filed on Jun. 28, 2017.

(51) Int. Cl.
*G16B 5/30* (2019.01)
*G06N 3/08* (2006.01)
(Continued)

(52) U.S. Cl.
CPC ............. *G16B 5/30* (2019.02); *G06K 9/6276* (2013.01); *G06N 3/08* (2013.01); *G16B 5/00* (2019.02);
(Continued)

(58) Field of Classification Search
CPC . G16B 5/30; G16B 5/00; G16B 40/00; G16B 40/20; G06K 9/6276; G06N 3/08; G06N 20/20
See application file for complete search history.

(56) References Cited

U.S. PATENT DOCUMENTS

| 7,430,475 B2* | 9/2008 | Imoto | G16B 25/10 435/6.13 |
| 2012/0041683 A1* | 2/2012 | Vaske | G16B 25/10 706/14 |

(Continued)

OTHER PUBLICATIONS

Abernathy et al., "Channeling in native microbial pathways: Implications and challenges for metabolic engineering," Biotechnology Advances 2017, 35, 805-814.
(Continued)

*Primary Examiner* — Santiago Garcia
(74) *Attorney, Agent, or Firm* — Sheppard, Mullin, Richter & Hampton LLP

(57) ABSTRACT

Disclosed herein are systems and methods for determining metabolic pathway dynamics using time series multiomics data. In one example, after receiving time series multiomics data comprising time-series metabolomics data associated a metabolic pathway and time-series proteomics data associated with the metabolic pathway, derivatives of the time series multiomics data can be determined. A machine learning model, representing a metabolic pathway dynamics model, can be trained using the time series multiomics data and the derivatives of the time series multiomics data, wherein the metabolic pathway dynamics model relates the time-series metabolomics data and time-series proteomics data to the derivatives of the time series multiomics data. The method can include simulating a virtual strain of the organism using the metabolic pathway dynamics model.

29 Claims, 15 Drawing Sheets

(51) Int. Cl.
| | |
|---|---|
| G06K 9/62 | (2022.01) |
| G16B 5/00 | (2019.01) |
| G16B 40/00 | (2019.01) |
| G16B 40/20 | (2019.01) |
| G06N 3/12 | (2006.01) |
| G06N 20/20 | (2019.01) |
| G06N 3/086 | (2023.01) |
| G06N 3/126 | (2023.01) |

(52) U.S. Cl.
CPC ............ *G16B 40/00* (2019.02); *G16B 40/20* (2019.02); *G06N 3/086* (2013.01); *G06N 3/126* (2013.01); *G06N 20/20* (2019.01)

(56) References Cited

U.S. PATENT DOCUMENTS

| | | | | |
|---|---|---|---|---|
| 2013/0259847 | A1* | 10/2013 | Vishnudas | C12Q 1/025 424/94.1 |
| 2017/0243083 | A1* | 8/2017 | Wang | G06V 20/40 |
| 2018/0357363 | A1* | 12/2018 | Frenkel | G16B 20/30 |
| 2019/0187048 | A1* | 6/2019 | Wood | G01N 21/65 |

OTHER PUBLICATIONS

Aguirre et al., "Dynamical effects of overparametrization in nonlinear models," Physica D 1995, 80, 26-40.
Alipanahi et al., "Predicting the sequence specificities of DNA- and RNA-binding proteins by deep learning," Nature Biotechnology 2015, 33(8), 831-838.
Alonso-Gutierrez et al., "Principal component analysis of proteomics (PCAP) as a tool to direct metabolic engineering," Metabolic Engineering 2015, 28, 123-133.
Arkin et al., "The DOE Systems Biology Knowledgebase (KBase)," bioRxiv 2016, 1-21.
Batth et al., A targeted proteomics toolkit for high-throughput absolute quantification of *Escherichia coli* proteins, Metabolic Engineering 2014, 26, 48-56.
Beller et al., "Natural products as biofuels and bio-based chemicals: fatty acids and isoprenoids," Natural Product Reports 2015, 32, 1508-1526.
Brunk et al., "Characterizing strain variation in engineered *E. coli* using a multi-omics based workflow," Cell Systems 2016, 2(5), 335-346.
Cardenas et al., "Metabolic engineering of Saccharomyces cerevisiae for the production of triacetic acid lactone," Metabolic Engineering 2014, 25, 194-203.
Chakrabarti et al., "Towards kinetic modeling of genome-scale metabolic networks without sacrificing stoichiometric thermodynamic and physiological constraints," Biotechnology Journal 2013, 8, 1043-1057.
Chen et al., "Promise of personalized omics to precision medicine," WIREs System Biology and Medicine 2013, 5, 73-82.
Chubukov et al., "Synthetic and systems biology for microbial production of commodity chemicals," NPJ Systems Biology and Applications 2016, 16009, 1-11.
Contador et al., "Ensemble modeling for strain development of l-lysine-producing *Escherichia coli*," Metabolic Engineering 2009, 11, 221-233.
Cornish-Bowden et al., "Fundamentals of Enzyme Kinetics Wiley-Blackwell," Analytical Biochemistry 2012, 231, 1-343.
Costa et al., "Hybrid dynamic modeling of *Escherichia coli* central metabolic network combining Michaelis-Menten and approximate kinetic equations," Biosystems 2010, 100, 150-157.
Costello et al., "A machine learning approach to predict metabolic pathway dynamics from time-series multiomics data," Nature Partner Journals 2018, 19, 1-14.
Daran-Lapujade et al., "The fluxes through glycolytic enzymes in *Saccharomyces cerevisiae* are predominantly regulated at post-transcriptional levels," Proc. Natl Acad. Sci. 2007,104(40), 15753-15758.

Dean et al., "Ensemble Modeling of hepatic fatty acid metabolism with a synthetic glyoxylate shunt," Biophysical Journal 2010, 98, 1385-1395.
Digel et al., "Acyl-CoA synthetases: fatty acid uptake and metabolic channeling," Molecular Cellular Biochemistry 2009, 326, 23-28.
Doerfler et al., "Granger causality in integrated GC-MS and LC-MS metabolomics data reveals the interface of primary and secondary metabolism," Metabolomics 2013, 9, 564-574.
Doudna et al., "The new frontier of genome engineering with CRISPR-Cas9," Science 2014, 346(6213), 1258096-1-1258096-9.
Dyar et al., "Circadian Metabolomics in Time and Space," Frontiers in Neuroscience 2017, 11(36), 1-10.
Esteva et al., "Dermatologist-level classification of skin cancer with deep neural networks," Nature 2017, 542, 115-118.
Fortman et al., "Biofuel alternatives to ethanol: pumping the microbial well," Trends in Biotechnology 2008, 26(7), 375-381.
Fuhrer et al., "High-throughput discovery metabolomics," Current Opinion in Biotechnology 2015, 31, 73-78.
Gardner, "Synthetic biology: from hype to impact," Trends in Biotechnology 2013, 31(3), 123-124.
George et al., "Correlation Analysis of Targeted Proteins and Metabolites to Assess and Engineer Microbial Isopentenol Production," Biotechnology and Bioengineering 2014, 111(8), 1648-1658.
George et al., "Metabolic engineering for the high-yield production of isoprenoid-based C5 alcohols in *E. coli*," Scientific Reports 2015, 5(11128), 1-12.
Gerber, "The dynamic microbiome," FEBS Letters 2014, 588, 4131-4139.
Gerosa et al., "Pseudo-transition Analysis Identifies the Key Regulators of Dynamic Metabolic Adaptations from Steady-State Data," Cell Systems 2015, 1, 270-282.
Ghosh et al., "$^{13}$C Metabolic Flux Analysis for Systematic Metabolic Engineering of *S. cerevisiae* for Overproduction of Fatty Acids," Frontiers in Bioengineering and Biotechnology 2016, 4(76), 1-10.
Grassegger et al., "The Data That Turned the World Upside Down," Motherboard 2017.
Grushkin, "The Rise and Fall of the Company That Was Going to Have Us All Using Biofuels," Fast Company 2012, https://www.fastcompany.com/3000040/rise-andfall-company-was-going-have-us-all-using-biofuels.
Hackett et al., "Systems-level analysis of mechanisms regulating yeast metabolic flux," Science 2016, 354(6311), aaf2786-1-aaf2786-15.
Hastie et al., "The Elements of Statistical Learning," Springer 2009, Second Edition.
Hatzimanikatis et al., "Effects of Spatiotemporal Variations on Metabolic Control: Approximate Analysis Using (Log)Linear Kinetic Models," Biotechnology and Bioengineering 1997, 54(2), 91-104.
Heijnen, "Approximative Kinetic Formats Used in Metabolic Network Modeling," Biotechnology and Bioengineering 2005, 91(5), 534-545.
Heinemann et al., "Real-Time Digitization of Metabolomics Patterns from a Living System Using Mass Spectrometry," Journal of the American Society of Mass Spectrometry 2014, 1755-1762.
Heinrich et al., "The Regulation of Cellular Systems," Springer 1996, 1-372.
Heintz-Buschart et al., "Integrated multi-omics of the human gut microbiome in a case study of familial type 1 diabetes," Nature Microbiology 2016, 2(16180), 1-14.
Henry et al., "Thermodynamics-Based Metabolic Flux Analysis," Biophysical Journal 2007, 92, 1792-1805.
Horn et al., "General Mass Action Kinetics," Archive for Rational Mechanics and Analysis 1972, 47, 81-116.
Ishii et al., "Multiple High-Throughput Analyses Monitor the Response of *E. coli* to Perturbations," Science 2007, 316, 593-597.
Karr et al., "A Whole-Cell Computational Model Predicts Phenotype from Genotype," Cell 2012, 150, 389-401.
Khodayari et al., "A genome-scale *Escherichia coli* kinetic metabolic model k-ecoli457 satisfying flux data for multiple mutant strains," Nature Communications 2016, 7(13806), 1-12.

(56) References Cited

OTHER PUBLICATIONS

Khodayari et al., "Succinate overproduction: A case study of computational strain design using a comprehensive *Escherichia coli* kinetic model," Frontiers in Bioengineering and Biotechnology 2015, 2(76), 85-95.
Khodayari et al., "A kinetic model of *Escherichia coli* core metabolism satisfying multiple sets of mutant flux data," Metabolic Engineering 2014, 25, 50-62.
Kosinski et al., "Private traits and attributes are predictable from digital records of human behavior," Proc. Natl Acad. Sci. 2013, 110, 5802-5805.
Lee et al., "Systems metabolic engineering of microorganisms for natural and non-natural chemicals," Nature Chemical Biology 2012, 8, 536-546.
Lewis et al., "Constraining the metabolic genotype-phenotype relationship using a phylogeny of in silico methods," Nature Reviews Microbiology 2012, 10, 291-305.
Lienert et al., "Synthetic biology in mammalian cells: next generation research tools and therapeutics," Nature Reviews Molecular Cell Biology 2014, 15, 95-107.
Lin et al., "Improving Fatty Acid Availability for Bio-Hydrocarbon Production in *Escherichia coli* by Metabolic Engineering," PLoS One 2013, 8(10), e78595.
Link et al., "Real-time metabolome profiling of the metabolic switch between starvation and growth," Nature Methods 2015, 12(11), 1091-1097.
Ljung "Approaches to Identification of Nonlinear Systems," Proceedings of the 29th Chinese Control Conference 2010, 1-5.
Ma et al., "Integrated Proteomic and Metabolomic Analysis of an Artificial Microbial Community for Two-Step Production of Vitamin C," PLoS One 2011, 6(10), e26108.
Martin et al., "A Method to Constrain Genome-Scale Models with $^{13}C$ Labeling Data," PLoS Computational Biology 2015, 11(9), e1004363.
Matsuoka et al., "Current status and future perspectives of kinetic modeling for the cell metabolism with incorporation of the metabolic regulation mechanism," Bioresources and Bioprocessing 2015, 2(4), 1-19.
Morrell et al., "The Experiment Data Depot: A Web-Based Software Tool for Biological Experimental Data Storage, Sharing, and Visualization," ACS Synthetic Biology 2017, 6, 2248-2259.
Muller et al., "Community-integrated omics links dominance of a microbial generalist to fine-tuned resource usage," Nature Communications 2014, 5(5603), 1-10.
Narayanasamy et al., "Integrated omics for the identification of key functionalities in biological wastewater treatment microbial communities," Microbial Biotechnology 2015, 8, 363-368.
National Research Council, "Industrialization of Biology: A Roadmap to Accelerate the Advanced Manufacturing of Chemicals," The National Academies Press 2015, 1-167.
Noor et al., "Pathway Thermodynamics Highlights Kinetic Obstacles in Central Metabolism," PLoS. Computational Biology 2014, 10(2), e1003483.
O'Brien et al., "Genome-scale models of metabolism and gene expression extend and refine growth phenotype prediction," Molecular Systems Biology 2013, 9(693), 1-13.
Olson et al., "Automating Biomedical Data Science Through Tree-Based Pipeline Optimization," arXiv:1601.07925v1 2016, 1-16.
Paeng et al., "A Unified Framework for Tumor Proliferation Score Prediction in Breast Histopathology," arXiv:1612.07180v1 2016, 1-11.
Pan et al., "A Survey on Transfer Learning," IEEE Transactions on Knowledge and Data Engineering 2009, 1345-1359.
Patel et al., "CircadiOmics: integrating circadian genomics, transcriptomics, proteomics and metabolomics," Nature Methods 2012, 9(8), 772-773.
Pedregosa et al., "Scikit-learn: Machine learning in Python," Journal of Machine Learning Research 2011, 12, 2825-2830.
Poplin et al., "Creating a universal SNP and small indel variant caller with deep neural networks," bioRxiv 2016, 1-10.
Price et al., "A wellness study of 108 individuals using personal, dense, dynamic data clouds," Nature Biotechnology 2017, 35(8), 747-756.
Rizk et al., "Ensemble modeling for aromatic production in *Escherichia coli*," PLoS One 2009, 4(9), e6903.
Ruder et al., "Synthetic Biology Moving into the Clinic," Science 2011, 333, 1248-1252.
Russo, "Special report: The birth of biotechnology," Nature 2003, 421 (6921), 456-457.
Sauer, "Metabolic networks in motion: $^{13}C$-based flux analysis," Molecular Systems Biology 2006, 2(62), 1-10.
Savageau et al., "Power-law approach to modeling biological systems: I. Theory," Journal of Fermentation Technology 1982, 60(3), 221-228.
Savitzky et al., "Smoothing and Differentiation of Data by Simplified Least Squares Procedures," Analytical Chemistry 1964, 36(8), 1627-1639.
Savoglidis et al., "A method for analysis and design of metabolism using metabolomics data and kinetic models: Application on lipidomics using a novel kinetic model of sphingolipid metabolism," Metabolic Engineering 2016, 37, 46-62.
Shah et al., "A microfluidics-based in vitro model of the gastrointestinal human-microbe interface," Nature Communications 2016, 7(11535), 1-15.
Silver et al., "Mastering the game of Go with deep neural networks and tree search," Nature 2016, 529, 484-489.
Slomovic et al., "Synthetic biology devices for in vitro and in vivo diagnostics," Proc. Natl Acad. Sci. 2015, 112(47), 14429-14435.
Stephens et al., "Big Data: Astronomical or Genomical?," PLoS Biology 2015, 13(7), 1-11.
Tan et al., "Metabolic ensemble modeling for strain engineers," Biotechnology Journal 2012, 7, 343-353.
Tang et al., "New Tools for Cost-Effective DNA Synthesis," Synthetic Biology, Elsevier 2013, 3-21.
Thrun et al., "Toward Robotic Cars," Communications of the ACM 2010, 53(4), 99-106.
Tompson et al., "Accelerating Eulerian Fluid Simulation With Convolutional Networks," arXiv 2017.
Tran et al., "Ensemble Modeling of Metabolic Networks," Biophysical Journal 2008, 95, 5606-5617.
Van Dien et al., "From the first drop to the first truckload: commercialization of microbial processes for renewable chemicals," Current Opinion Biotechnology 2013, 24, 1061-1068.
Villaverde et al., "Reverse engineering and identification in systems biology: strategies, perspectives and challenges," Journal of the Royal Society Interface 2014, 11(May 5, 2013), 1-16.
Watson et al., "Genetical Implications of the Structure of Deoxyribonucleic Acid," Nature 1953, 4361, 965-967.
Weaver, "Towards predictive metabolic engineering: kinetic modeling and experimental analysis of a heterologous mevalonate pathway in *E. coli*," Dissertation UC Berkeley, 2013.
Wiechert, "$^{13}C$ Metabolic Flux Analysis," Metabolic Engineering 2011, 3, 195-206.
Wu et al., "Google's Neural Machine Translation System: Bridging the Gap between Human and Machine Translation," arXiv:1609.08144v1 2016, 1-23.
Xu et al., "Genome-scale metabolic network modeling results in minimal interventions that cooperatively force carbon flux towards malonyl-CoA," Metabolic Engineering 2011, 13(5),578-587.
Yang et al., "Clostridium thermocellum ATCC27405 transcriptomic, metabolomic and proteomic profiles after ethanol stress," BMC Genomics 2012, 13(336), 1-17.

\* cited by examiner $$\dot{m} = f(m, p)$$

| Prediction (output) | | | | | | | Features (Input) | | | | | |
|---|---|---|---|---|---|---|---|---|---|---|---|---|
| $\dot{\tilde{m}}_1(t_1)$ | ... | $\dot{\tilde{m}}_n(t_1)$ | ... | $\dot{\tilde{m}}_1(t_T)$ | ... | $\dot{\tilde{m}}_n(t_T)$ | $\tilde{m}(t_1), \tilde{p}(t_1)$ | ... | $\tilde{m}(t_1), \tilde{p}(t_1)$ | ... | $\tilde{m}(t_T), \tilde{p}(t_T)$ | $\tilde{m}(t_T), \tilde{p}(t_T)$ |

FIG. 3

$$\frac{d[A-CoA]}{dt} = \frac{K_{1,1}[AtoB][A-CoA]}{K_{1,2} + K_{1,3}[A-CoA]} - \frac{K_{2,1}[HMGS][A-CoA][AA-CoA]}{K_{2,2}[AA-CoA] + K_{2,3}[A-CoA] + K_{2,4}[A-CoA][AA-CoA]k_{s3}}$$

$$\frac{d[AA-CoA]}{dt} = \frac{K_{1,1}[AtoB][A-CoA]}{K_{1,2}K_{1,3}[A-CoA]} - \frac{K_{2,1}[HMGS][A-CoA][AA-CoA]}{K_{2,2}[AA-CoA] + K_{2,3}[A-CoA] + K_{2,4}[A-CoA][AA-CoA]k_{s3}}$$

$$\frac{d[HMG-CoA]}{dt} = \frac{K_{2,1}[HMGS][A-CoA][AA-CoA]}{K_{2,2}[AA-CoA] + K_{2,3}[A-CoA] + K_{2,4}[A-CoA][AA-CoA]k_{s3}} - \frac{K_{3,1}[HMGR][HMG-CoA]}{K_{3,2}[A-CoA] + K_{3,3}[AA-CoA] + K_{3,4}[HMG-CoA] + K_{3,5}}$$

$$\frac{d[Mev]}{dt} = \frac{K_{3,1}[HMGR][HMG-CoA]}{K_{3,2}[A-CoA] + K_{3,3}[AA-CoA] + K_{3,4}[HMG-CoA] + K_{3,5}} - \frac{K_{4,1}[MK][Mev]}{K_{4,2}[GPP] + K_{4,3}[MevP] + K_{4,4}[Mev] + K_{4,5}}$$

$$\frac{d[MevP]}{dt} = \frac{K_{4,1}[MK][Mev]}{K_{4,2}[GPP] + K_{4,3}[MevP] + K_{4,4}[Mev] + K_{4,5}} - \frac{K5,1[PMK][MevP]}{K_{5,1} + [MevP]}$$

$$\frac{d[MevPP]}{dt} = \frac{K5,1[PMK][MevP]}{K_{5,1} + [MevP]} - \frac{K_{6,1}[PMD][MevPP]}{K_{6,2}[MevP] + K_{6,3}[Mev] + K_{6,4}[MevPP] + K_{6,5}}$$

$$\frac{d[IPP]}{dt} = \frac{K_{6,1}[PMD][MevPP]}{K_{6,2}[MevP] + K_{6,3}[Mev] + K_{6,4}[MevPP] + K_{6,5}} - \frac{K_{7,1}[IDI][IPP]}{K_{7,2} + [IPP]}$$

$$\frac{d[DMAPP]}{dt} = \frac{K_{7,1}[IDI][IPP]}{K_{7,2} + [IPP]} - \frac{K_{8,1}[GPPS][IPP][DMAPP]}{K_{8,2} + K_{8,3}[IPP] + K_{8,4}[DMAPP] + [IPP][DMAPP]}$$

$$\frac{d[GPP]}{dt} = \frac{K_{8,1}[GPPS][IPP][DMAPP]}{K_{8,2} + K_{8,3}[IPP] + K_{8,4}[DMAPP] + [IPP][DMAPP]} - \frac{K_{9,1}[LS][GPP]}{K_{9,2} + [GPP]}$$

$$\frac{d[Limonene]}{dt} = \frac{K_{9,1}[LS][GPP]}{K_{9,2} + [GPP]}$$

FIG. 7

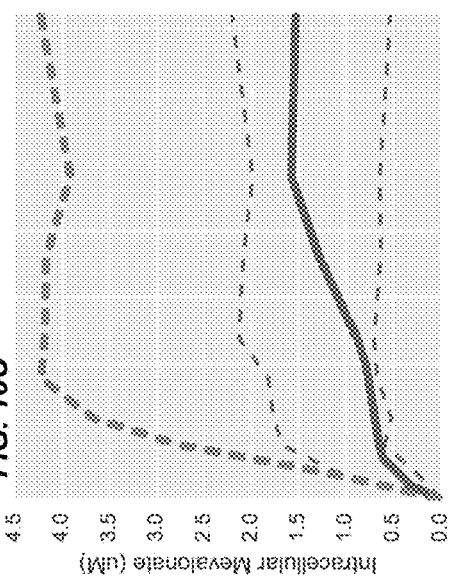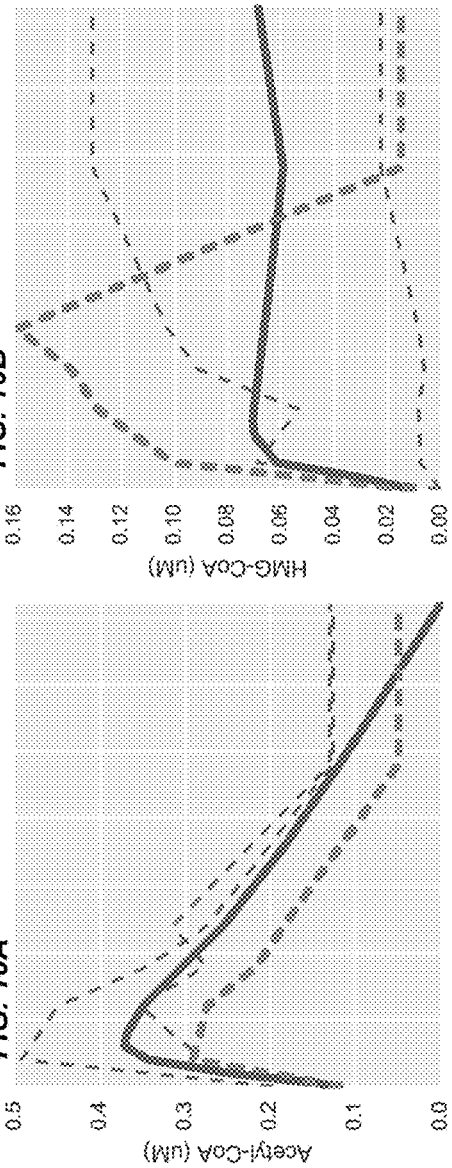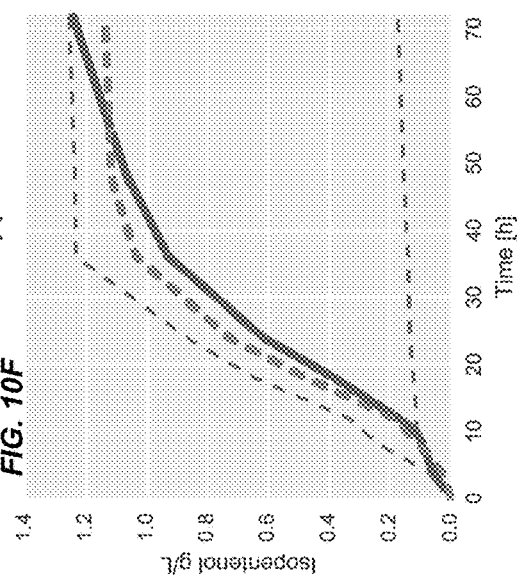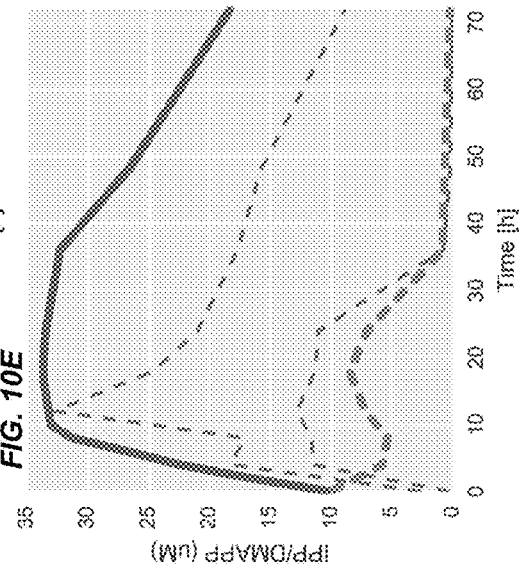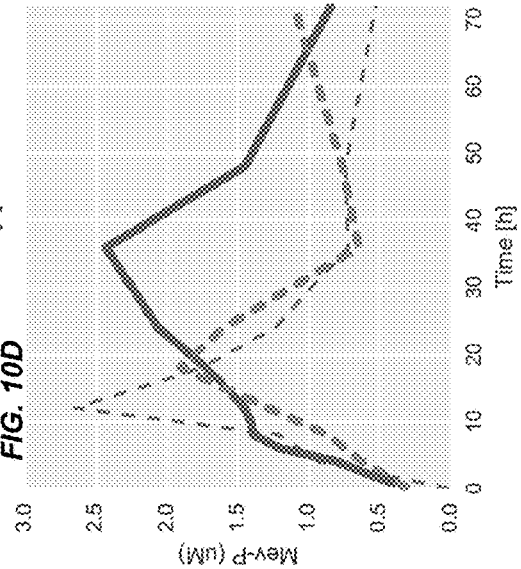
FIG. 10A FIG. 10B FIG. 10C FIG. 10D FIG. 10E FIG. 10F
Prediction of Isopentenol Strain Dynamics
Red — Training Set Data  Green — Test Data  Blue — Machine Learning Model Prediction

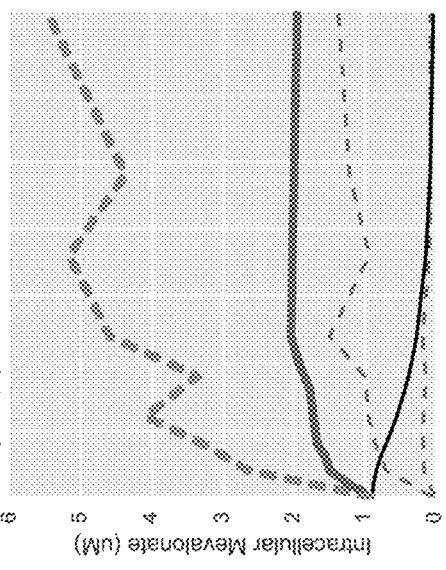
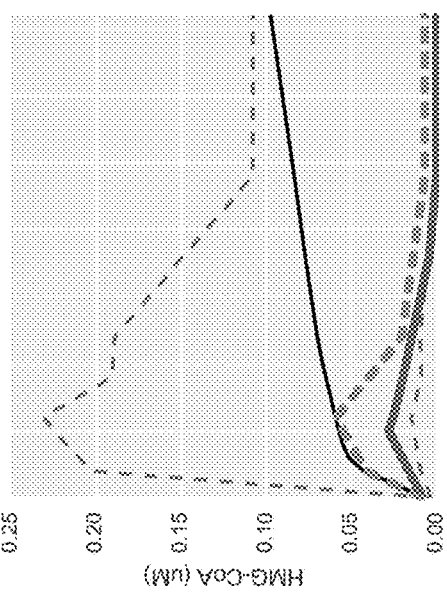
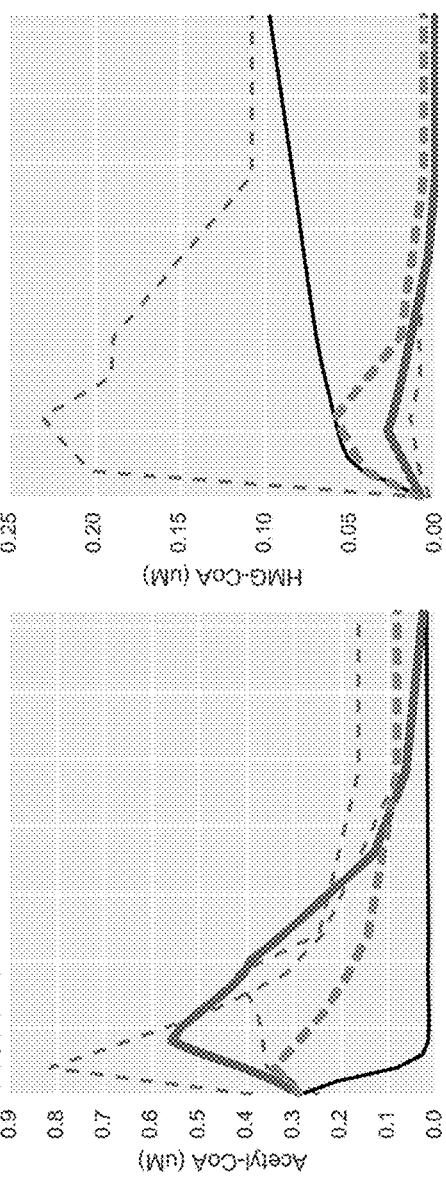
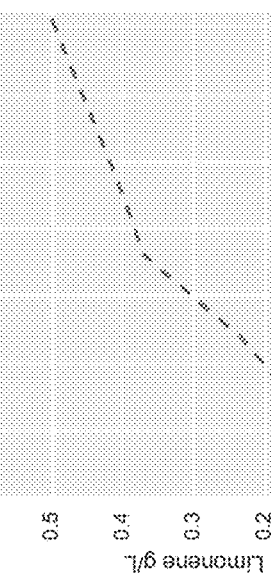
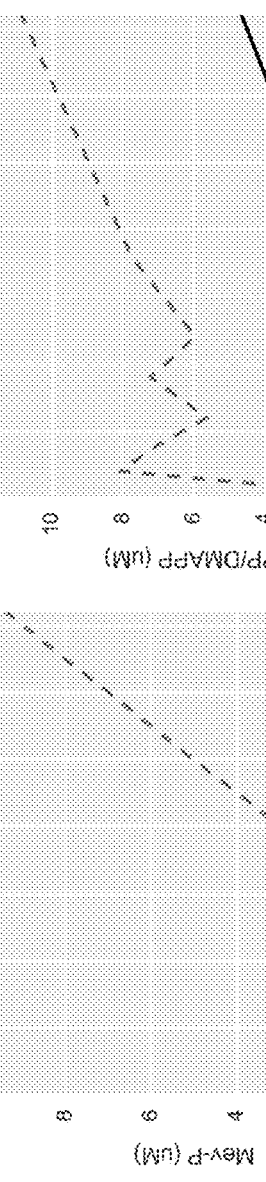
FIG. 11A FIG. 11B FIG. 11C FIG. 11D FIG. 11E FIG. 11F
Prediction of Limonene Strain Dynamics
Red — Training Set Data  Green — Test Data  Blue — Machine Learning Model Prediction  Black — Kinetic Model Prediction

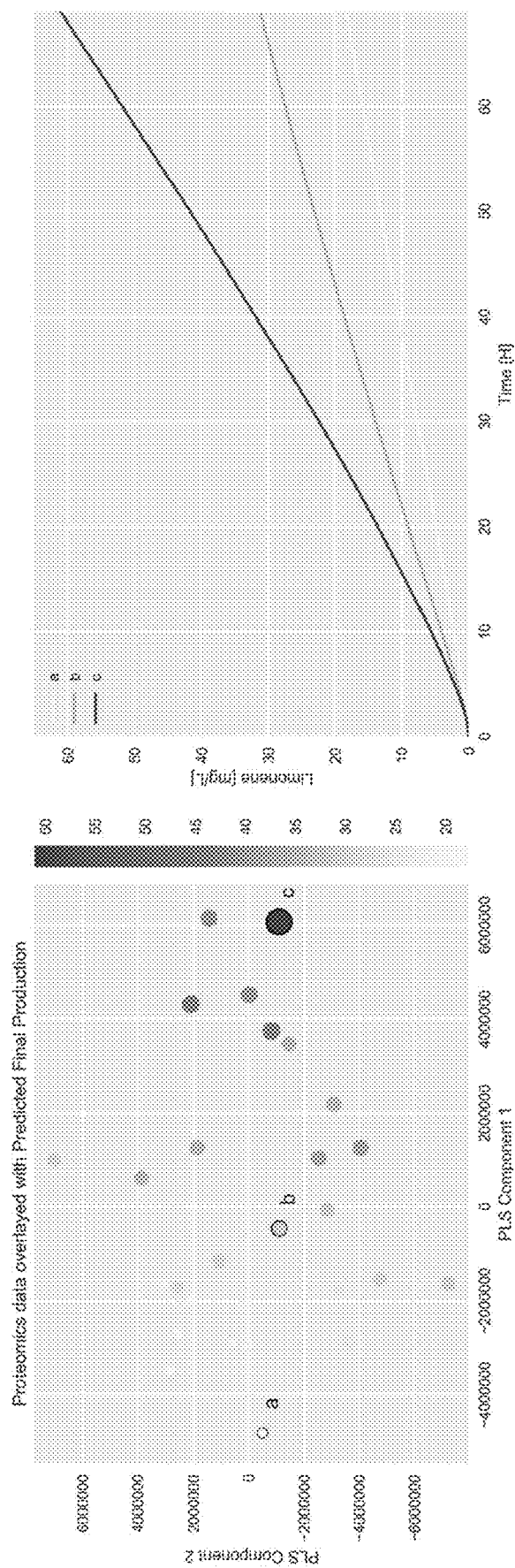

US 11,636,917 B2

SIMULATING THE METABOLIC PATHWAY DYNAMICS OF AN ORGANISM

CROSS-REFERENCE TO RELATED APPLICATIONS

This application is a non-provisional application of and claims priority to U.S. Provisional Patent Application No. 62/526,278 filed on Jun. 28, 2017, hereby incorporated by reference in its entirety.

STATEMENT REGARDING FEDERALLY SPONSORED R&D

This invention was made with government support under grant no. DE-AC02-05CH11231 awarded by the U.S. Department of Energy. The government has certain rights in the invention.

BACKGROUND

Field

The present disclosure relates generally to the field of computational biology, and more particularly to determining dynamics of metabolic pathways.

Description of the Related Art

The last few decades have witnessed a revolutionary transformation in the biological sciences, which have evolved from a focus on explanation and classification of biological entities to acquiring the capability of changing their instruction set (DNA). However, while the capability to create new designs improves fast, the ability to predict the outcomes of the designs is still extremely limited, and this hinders the creation of, and investment, in new biological applications.

Advances in synthetic biology have enabled biological entities to be characterized, modeled, and modified (e.g., using the CRISPR methods). To design biological entities efficiently, the results of the designs have to be determined or predicted using particular computational models. Large amounts of high quality data can enable models to be parametrized and tested. However, traditional models, such as models based solely on Michaeles-Menten kinetics, may be insufficient for predicting biological behavior accurately and efficiently.

SUMMARY

Disclosed herein are systems and methods for determining metabolic pathway dynamics using time-series multiomics data. In one example, the method includes: receiving time-series multiomics data comprising time-series metabolomics data associated a metabolic pathway and time-series proteomics data associated with the metabolic pathway; determining derivatives of the time-series multiomics data; training a machine learning model, representing a metabolic pathway dynamics model, using the time-series multiomics data and the derivatives of the time-series multiomics data, wherein the metabolic pathway dynamics model relates the time-series metabolomics data and time-series proteomics data to the derivatives of the time-series multiomics data; and simulating a virtual strain of the organism using the metabolic pathway dynamics model.

In another example, the system includes: computer-readable memory storing executable instructions; and one or more hardware processors programmed by the executable instructions to perform a method comprising: receiving time-series multiomics data comprising time-series metabolomics data associated a metabolic pathway and time-series proteomics data associated with the metabolic pathway; determining derivatives of the time-series multiomics data; training a machine learning model, representing a metabolic pathway dynamics model, using the time-series multiomics data and the derivatives of the time-series multiomics data, wherein the metabolic pathway dynamics model relates the time-series metabolomics data and time-series proteomics data to the derivatives of the time-series multiomics data; and simulating a virtual strain of the organism using the metabolic pathway dynamics model.

Disclosed herein are systems and methods for simulating the pathway dynamics of a virtual strain of an organism. In one example, the method includes: receiving time-series multiomics data comprising a first time-series multiomics data associated a metabolic pathway and a second time-series multiomics data associated with the metabolic pathway; determining derivatives of the first time-series multiomics data; training a machine learning model, representing a metabolic pathway dynamics model, using the first time-series multiomics data, the derivatives of the first time-series multiomics data, and the second time-series multiomics data, wherein the metabolic pathway dynamics model relates the first time-series multiomics data and the second time-series multiomics data to the derivatives of the first time-series multiomics data; and simulating a virtual strain of the organism using the metabolic pathway dynamics model.

In another example, the system includes computer-readable memory storing executable instructions; and one or more hardware processors programmed by the executable instructions to perform a method comprising: receiving time-series multiomics data comprising time-series metabolomics data associated a metabolic pathway and time-series proteomics data associated with the metabolic pathway; determining derivatives of the time-series multiomics data; training a machine learning model, representing a metabolic pathway dynamics model, using the time-series multiomics data and the derivatives of the time-series multiomics data, wherein the metabolic pathway dynamics model relates the time-series metabolomics data and time-series proteomics data to the derivatives of the time-series multiomics data; and simulating a virtual strain of the organism using the metabolic pathway dynamics model.

BRIEF DESCRIPTION OF THE DRAWINGS

FIG. 3 shows a table of inputs and outputs to the machine learning model. In one embodiment, the core of the method consists in using one or more machine learning methods to predict the functional relationship between the metabolite derivative and proteomics and metabolomics data, substituting the traditional Michaelis-Menten relationship. The machine learning approach involved training a model for each metabolite that is being predicted (Table 1). Each model took all the measured metabolites and proteins at a particular time $t_i$ as input. The prediction it provided as an output is the derivative of one of the pathway metabolites at the same time instant. The symbols $\hat{m}$ and $\hat{p}$ denote the experimentally measured metabolomic and proteomics measurements, respectively.

FIG. 7 shows differential equations for a limonene pathway kinetic Michaelis-Menten model. This kinetic model was compiled from sources in the BRaunschweig ENzyme DAtabase (BRENDA) database. This model includes ten nonlinear ordinary differential equations, which describe the concentration for each metabolite in the pathway. The dynamics of this Michaelis-Menten model are complex enough to pose a significant challenge for machine learning techniques. This model was used to: (1) compare its predictions with machine learning predictions, and (2) generate simulated data sets to check scaling dependencies with the amount of time series used for training of machine learning processes. The machine learning method can be used to supplement, complement, or substitute these Michaelis-Menten expressions (see FIG. 3). Kinetic constants were left as free parameters when fitting experimental data shown in FIGS. 11A-11F.

FIGS. 10A-F show line graphs illustrating that the machine learning method produced good predictions of metabolite time series from proteomics data for the isopentenol producing E. coli strain. The measured metabolomics and proteomics data for the highest and lowest producing strains (training set data, red line) were used to train a model and learn the underlying dynamics (FIG. 2). The model was then tested by predicting the metabolite profiles (blue line) for a strain the model has never seen (medium producing strain, test data in green). A perfect prediction (blue line) would perfectly track the test data set (green line). Reasonable qualitative agreement was achieved even with only two time-series (strains) as training data. From a purely quantitative perspective, the average error could be improved: the total RMSE for the strain predictions was 40.34, which can be translated to 149.2% average error. However, for some metabolites the predictions quantitatively reproduced the measured data: Acetyl-CoA and isopentenol (the final product, which may be highly relevant for guiding bioengineering). For some metabolites (mevalonate, mevalonate phosphate and IPP/DMAPP), the model qualitatively reproduced the metabolite patterns, with scaling factors that may be improved. For HMG-CoA, the model can be further improved in the predictions of the metabolite concentration over time both quantitatively and qualitatively.

FIGS. 11A-11F show line graphs illustrating that the machine learning method outperformed the handcrafted kinetic model for the limonene producing E. coli strain. The only metabolite for which the kinetic model (black line) provided a better fit than the machine learning method (blue line) was mevalonate phosphate, although both methods appeared to track limonene (final product) production fairly well. The machine learning approach provided acceptable quantitative fits for Acetyl-CoA, HMG-CoA, and limonene, a qualitative description of metabolite behavior missing the scale factor for mevalonate, and did not provide either a qualitative description nor quantitatively accurate fit for mevalonate phosphate and IPP/DMAPP. As in FIGS. 10A-10F, the experimentally measured profiles corresponded to high, low and medium producers of limonene. The training sets were the low and high producers (in red), and the model was used to predict the concentrations for the medium producing strain (in green). Kinetic constants for the handcrafted kinetic model in FIG. 7 were left as free parameters when fitting the experimental data.

FIG. 14A is a bar chart showing the success rate in predicting the relative production order (i.e., which strain produced most, which one produced least and which one was a medium producer) for groups of three time series (strains) randomly chosen from a pool of 10,000 strains, as a function of training data set size (strains). For 100 data sets, the failure rate to predict the top producer was <10%. For ten data sets the success rate was ~80%, which was reliable enough to guide engineering efforts. The horizontal line provided the rate of success (⅙) if order is chosen randomly. FIG. 14B is a plot showing that prediction of limonene production was extremely accurate for the case of a training data set comprised of 100 time-series (strains). These data shows that the machine learning model predictions were accurate enough to guide pathway design if enough training data is available.

FIG. 15A is a plot FIG. 15B is a line graph that show that a machine learning (ML) approach can be used to produce biological insights. FIG. 15A shows the final position in the proteomics phase space (similarly to the PCAP approach) for 50 strains generated by the ML process by learning from the Michaelis-Menten kinetic model (FIG. 7) used as ground truth. Final limonene production is given by circle size and color. The PLS process found directions in the proteomics phase space that best align with increasing limonene production (component 1). Traveling in proteomics phase space along that direction (which involved overexpression of LS and underexpression of AtoB, PMD, and Idi, see Table 2) created strains with higher limonene production. The ML approach not only produced biological insights to increase production but also predicted the expected concentration as a function of time for limonene and all other metabolites, generating hypotheses that can be experimentally tested (right panel).

DETAILED DESCRIPTION

Figure 1:
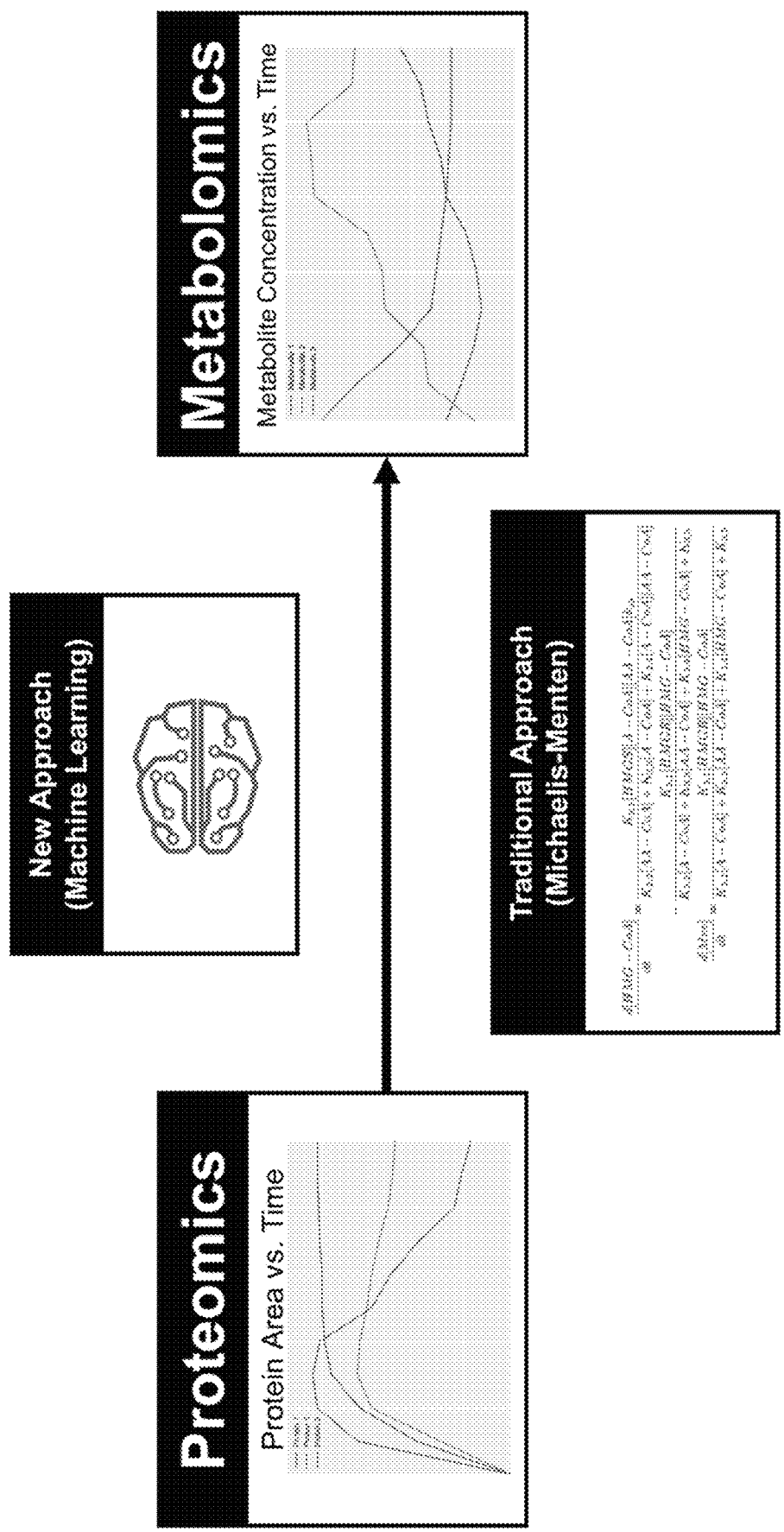
FIG. 1 is a schematic illustration comparing methods of kinetic modeling based on ordinary differential equations and based on machine learning. The machine learning (ML) method uses time-series proteomics data to predict time-series metabolomics data (FIG. 2). The machine learning approach can complement, or supplement, a method based on ordinary differential equations where the change in metabolites over time is given by Michaelis-Menten kinetics (FIGS. 4 and 7). The machine learning method disclosed herein uses a time series of proteomics and metabolomics data to feed machine learning processes in order to predict pathway dynamics (Eq. (1) and FIG. 3). The machine learning method may require more data for training and/or make more accurate predictions. The method of the disclosure may be automatically applied to any pathway or host, thus leverages systematically new data sets to improve accuracy, and captures dynamic relationships which are unknown experimentally or have a different dynamic form Michaelis-Menten kinetics.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Disclosed herein are systems and methods for accurately and efficiently determining dynamics of a metabolic pathway. In one embodiment, the metabolic pathway is a heterologous metabolic pathway. In one embodiment, the method comprises determining or inferring the dynamics of a metabolic pathway using time series proteomics and metabolomics data. The genomic and post-genomic revolutions have generated orders of magnitude more data than biological researchers can interpret, in the form of functional genomics data (transcriptomics, proteomics, metabolomics and fluxomics). One method described herein leverages these large sets of functional genomics data to predict metabolite concentration time series from the knowledge of protein levels.

The method can include determining a computational model of a particular organism based on the dynamics of one or more metabolic pathways in the organism using time-series data. In one embodiment, the model is not based on Michaelis-Menten kinetics which is based on a plurality of differential equations. The model may supplement, or complement, a model based on Michaelis-Menten kinetics. The model can be scalable to genome-scale time-series data. The model can be based on a plurality of relationships or expressed as a plurality of equations. The right hand side of the equation (see Eq. (3) below) can be estimated through machine learning methods as a function of metabolite and protein concentrations. In one implementation, the machine learning model can be a supervised machine learning model.

In one embodiment, the method comprises accurately determining or estimating time-series data that can be used to train a machine learning model with an accurate model performance. The amount of time-series data required for achieving good model performance can be estimated based on simulated data of one or more metabolic pathways. In one example, the simulated data is proteomics or metabolomics data, such as the mevalonate pathway engineered in E. coli.

In one embodiment, the method can include determining an amount of time-series data sufficient for determining an accurate model with predetermined accuracy. In one embodiment, the method can include evaluating the simulated data against real data for strains of an organism of interest. For example, the organism may be engineered to produce certain compounds, such as limonene, isopentenol, bisaboline, or organic molecules of interest. In one embodiment, the method comprises predicting production of a medium titer strain using time-series data for high and low producing strains as training sets. In one embodiment, the method comprises receiving or generating sufficient time-series data for determining the dynamics of complex coupled nonlinear systems relevant to metabolic engineering.

Overview

Increasingly computational biology is focusing on large scale modeling of dynamical systems as a way to better predict phenotype from genotype. Modeling of these complex systems has been made possible in part due to advances in high throughput data collection. For example, transcriptomics data volume has a doubling rate of seven months. The collection of large data sets has allowed for fitting of increasing complex parametric models. As models become more complex, fitting and troubleshooting these models can require more time from domain experts.

Disclosed herein are systems and methods for determining complex cellular dynamics, including non-linear dynamics, from observed data within the organism. The systems and methods can be used to approximate the dynamical behavior of these biological systems. In one example, the method can utilize non-linear identification methods. The model determined can be used for design and optimization of synthetic pathways. Some or all of the relevant dynamic quantities used to learn the models can be time series observations. The model learned can be used for predicting the dynamic behavior of a system from proteomics data specific to a metabolic subnetwork of interest. The methods disclosed herein can be scalable, resulting in enhanced predictive capacity.

Data Driven Model Creation

Embodiments relate to systems and method for combining machine learning and multiomics data (such as proteomics and metabolomics data) to effectively predict pathway dynamics of a living organism in an automated manner. The system may not assume any particular interactions, but rather implicitly chooses or models the most predictive interactions.

Biological Modeling of Large Metabolic Systems Involving Complex Dynamics

Figure 2:
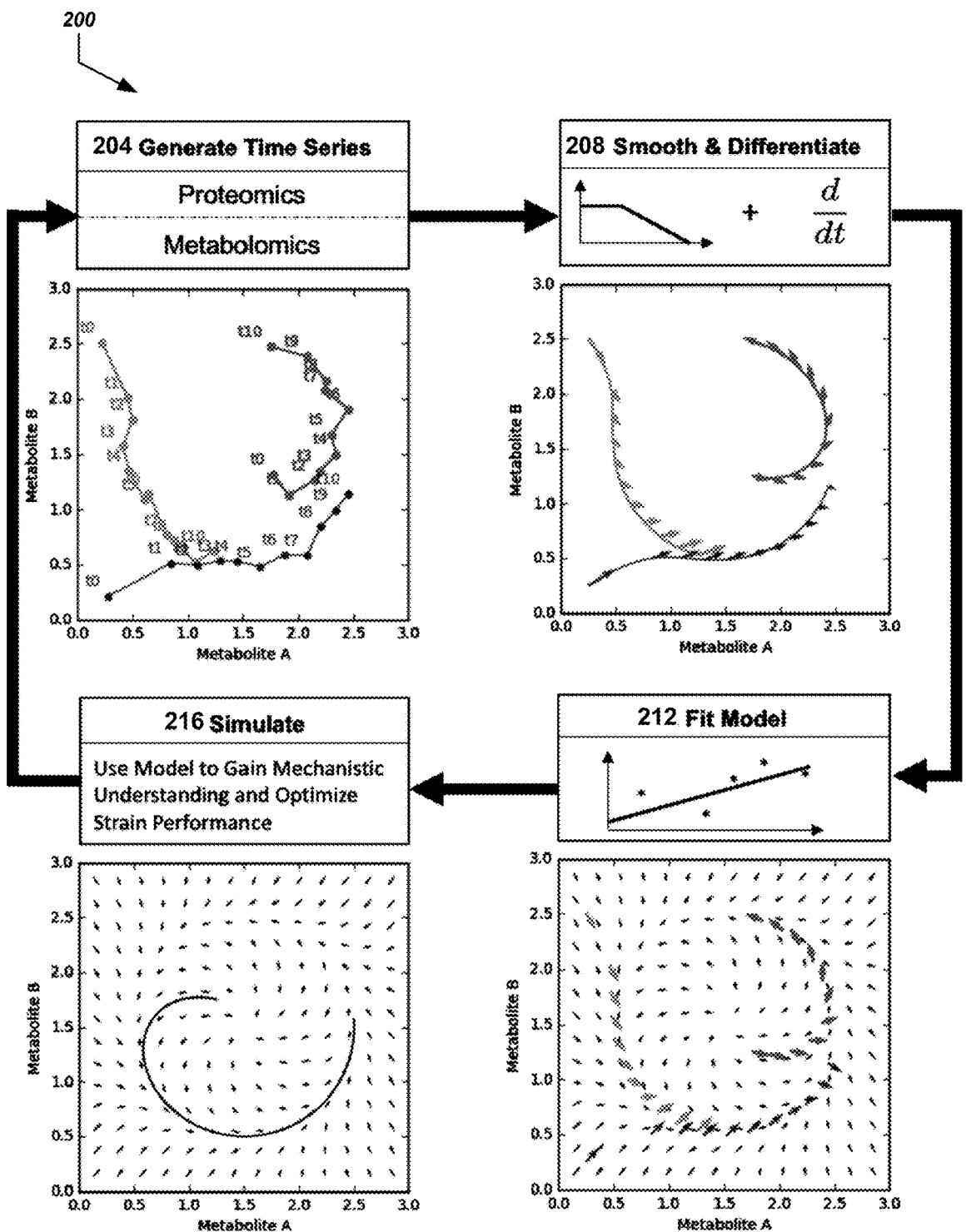
FIG. 2 shows a schematic illustration of a method for learning metabolic pathway dynamics from time series proteomics and metabolomics data. The method can be cyclic such that the metabolic system dynamics can be learned from time-series proteomics and metabolomics data, which can then be used to suggest new strain designs. At block 204, experimentally, time-series proteomics and metabolomics data are acquired for several strains of interest (time-series proteomics and metabolomics data from three strains of interest are represented by the three lines.). These data are represented in a metabolomics phase space, with an axis corresponding to each measured metabolite. At block 208, the time-series data traces are smoothed and differentiated (FIG. 5). The derivatives can be used as the training data to derive the relationship between metabolomics and proteomics data and the metabolite change (FIG. 3, Eq. (1)). At block 212, the state derivative pairs are fed into a machine learning process, such as a supervised machine learning process. The machine learning process learns and generalizes the system dynamics from the examples provided by each strain. At block 216, the model can then be used to simulate virtual strains and explore the metabolic space looking for mechanistic insight or valuable designs (such as commercially valuable designs). This process can then be repeated using the model to create new strains, which can further improve the accuracy of the dynamic model in the next round.

Disclosed herein are embodiments of a method for modeling metabolic pathway dynamics involving a machine learning (ML) approach (FIGS. 1 and 2). The function that determines the rate of change for each metabolite from protein and metabolite concentrations may be directly learned from training data (Eq. (1) and FIG. 3), without presuming any specific relationship.

This machine learning-based approach may provide a faster development of predictive pathway dynamics models since all required knowledge (regulation, host effects, etc.) may be inferred from experimental data, instead of arduously gathered and introduced by domain experts (see below for an example). In this way, the method provides a general approach, valid even if the host is poorly understood and there is little information on the heterologous pathway, and provides a systematic way to increase prediction accuracy as more data is added. This method may obtain better predictions than the traditional Michaelis-Menten approach. For example, the ML-based method may generate better predictions than a model based on Michaelis-Menten kinetics for the limonene and isopentenol producing pathways studied here (FIG. 4) using only two times series, corresponding to data generated by two strains. The prediction performance of the ML-based model may improve as more time-series data is added. The new method was found to be accurate enough to drive bioengineering efforts to create modified strains. The disclosed methods are scalable to genome-scale models and/or generally applicable to other types of data (e.g., transcriptomics) or dynamic systems (e.g., microbiome dynamics).

Disclosed herein are methods that use protein levels of an organism to predict times series of metabolite concentrations. Understanding this type of pathway dynamics allows an accurate prediction of the behavior of the pathway. This also may allow the reliable design of specific biological systems, such as strains bioengineered to produce particular chemical products. Embodiments may automatically learn these pathway dynamics from previously obtained metabolomics and proteomics data using machine learning approaches. For example, the method may include receiving sets of proteomics and metabolomics data collected for several strains of one or more organisms of different species and then applying a supervised learning process to the time-series data and its derivatives to predict metabolite time-series data from the proteomics data. This model can then be tested for new strains with improved predictive ability.

Supervised Learning of Metabolic Pathway Dynamics

Assume there are q sets of time series metabolite $\tilde{m}^i[t]\in \mathbb{R}^n$ (FIG. 5) and protein $\tilde{p}^i[t]\in \mathbb{R}^l$ observations at times $T=[t_1, t_2, \ldots, t_s]\in \mathbb{R}_+^s$. The superscript $i\in\{1, \ldots, q\}$ indicates the time-series index (strain), and $\tilde{m}[t]=[\tilde{m}_1[t], \ldots, \tilde{m}_n[t]]^T$ and $\tilde{p}[t]=[\tilde{p}_1[t], \ldots, \tilde{p}_n[t]]^T$ are vectors of measurements at time t containing concentrations for the n metabolites and l proteins considered in the model. The number of observation time points should be dense enough to capture the dynamic behavior of the system.

Figure 5:
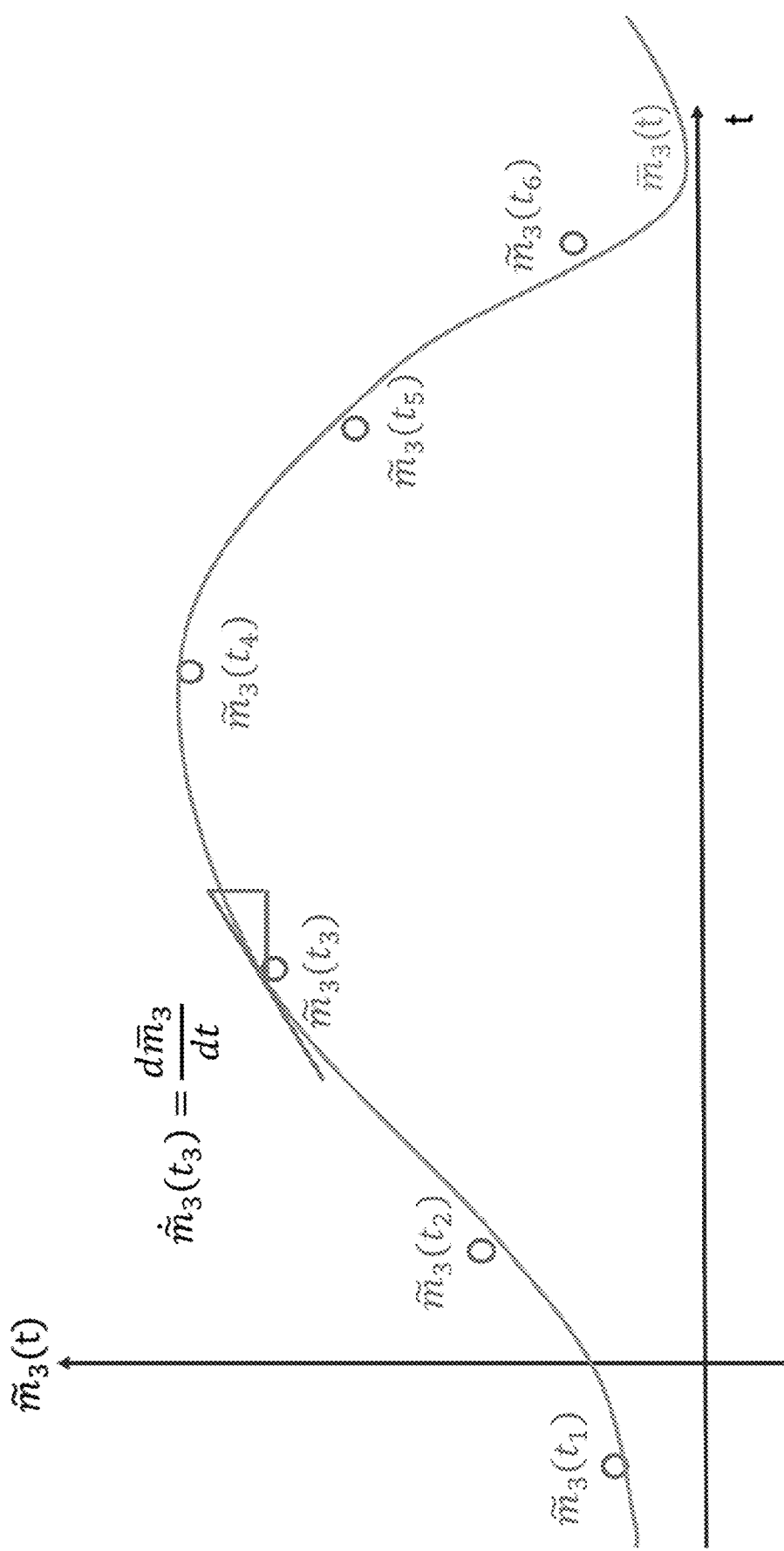
FIG. 5 is a line plot showing computing derivative from metabolomics training data. A set of data points for a particular metabolite were used. In this case, $\hat{m}_3$ had been measured at six time points. An interpolated and smoothed time series was created from the measurements, $\hat{m}_3$ (t), to reduce the noise of the signal and smooth the resulting derivative. The derivative of the time series was estimated by taking the derivative of the smoothed line at the time point of interest.

Assume that the underlying continuous dynamics of the system, which generates these time-series observations, can be described by coupled nonlinear ordinary differential equations of the general type used for kinetic modeling:

$$\dot{m}=f(m(t),p(t)), \quad (1)$$

where m and p are vectors that denote the metabolite and protein concentrations. The function $f: \mathbb{R}^{n+l} \to \mathbb{R}^n$ encloses all the information on the system dynamics. Deriving these dynamics from the time-series data can be formulated as a supervised learning problem where the function $f$ is learned through machine learning methods, which predict the relationship between metabolomics and proteomics concentrations (input features, see FIG. 3) and the metabolite time derivative $\dot{m}(t)$ (output). In order to provide the training data set for this problem, the metabolite time derivative $\dot{m}$ can obtained from the times-series data $\tilde{m}(t)$, as shown in FIG. 5.

In order to parametrize the machine learning process, the following optimization problem can be solved (such as through scikit-learn):

Supervised Learning of Metabolic Dynamics. Find a function $f$ which satisfies:

$$\operatorname*{argmin}_{f} \sum_{i=1}^{q}\sum_{t\in T} \left\| f(\tilde{m}^i[t], \tilde{p}^i[t]) - \dot{\tilde{m}}^i(t) \right\|^2. \quad (2)$$

Finding the function $f$ can be considered equivalent to finding the metabolic dynamics, which describe the time-series data provided. Once the dynamics are learned, the behavior of the metabolic pathway can be predicted by solving an initial value problem (Eqs. (3) and (4)).

Learning System Dynamics from Time-Series Data

The methods for determining dynamics of metabolic pathways disclosed herein can include using machine learning methods to predict the functional relationship between the metabolite derivative and proteomics and metabolomics data. The methods can include substituting the Michaelis-Menten relationship (Eq. (1), FIG. 3 and FIG. 7). The first step can involve creating a training set comprising sets of proteomics and metabolomics data and their corresponding derivatives (FIG. 3). This can include computing the derivatives of the metabolite concentration time-series data. Because the time-series data may be subject to measurement noise, in some embodiments the derivatives must be carefully estimated. The second step involves finding the best performing regression technique, among the many possibilities available. Finally, once the best performing regression technique is found and cross-validated, it can be used to predict metabolite concentrations given initial time points. The complete code to implement these steps is provided in github.

Construction of the Training Data Set

In order to train a machine learning model, a suitable training set has to be created. The trained machine learning model may take in metabolite and protein concentrations at a particular point in time and return the derivative of the metabolite concentrations at the same time point (FIG. 3). The observations provide the inputs to the model, $\tilde{m}^i[t]$ and $\tilde{p}[t]$. In order to have examples of correct outputs for supervised learning, the derivatives of the metabolite time-series data, $\dot{\tilde{m}}^i(t)$, can be esimated (FIG. 5).

Naively computing the derivative of a noisy signal may amplify the noise and make the result unusable. Derivatives of noisy signals, like those obtained from experiments, may require extra effort to estimate. In order to estimate the time derivatives on time series of real data obtained from Brunk et al. (Characterizing strain variation in engineered *E. coli* using a multiomics-based workflow. *Cell Syst.* 2, 335-346 (2016); the content of which is incorporated herein by reference in its entirety. Data is available at the code repository: github.com/JBEI/KineticLearning) accurately, a Savitzky-Golay filter (Smoothing and differentiation of data by simplified least squares procedures. *Anal. Chem.* 36, 1627-1639 (1964); the content of which is incorporated herein in its entirety) was applied to the noisy time-series data to find a smooth estimate of the data (FIG. 5). This smooth function estimate can then be used to compute a more accurate estimate of the derivative. The derivative estimate of the signal can be computed using a central difference scheme from the filtered experimental data. Specifically, the Savitzky-Golay filter can be used with a filter window of 7 and a polynomial order of 2. The derivative estimate, $\dot{\tilde{m}}^i(t)$ can be computed for all time points in T and time series i. This results in a training example associated with each time point in every time series.

In one implementation, all relevant metabolites are measured and the system may be assumed to have no unmeasured memory states. In other words, the present set of metabolite and protein measurements completely determines the metabolite derivatives at the next time instant. If this assumption does not hold practically, a limited time history of proteins and metabolites can be used to predict the derivative at the next time instant. This assumption produces good predictions for some metabolic pathways, such as those described herein.

Model Selection

In one implementation, the model selection process can be implemented using a meta-learning package in python called Tree-based Pipeline Optimization Tool (TPOT; available at epistasislab.github.io/tpot/). Once the training data set is established, a machine learning model can be selected to learn the relationship between input and outputs (FIG. 3). TPOT uses genetic processes to find a model with the best cross-validated performance on the training set. Cross validation techniques may be used to score an initial set of models. The best performing models may be mated to form a new population of models to test. This process may be repeated for a fixed number of generations and the best performing model may be returned to the user. If desired, the search space for model selection can be specified before execution of the TPOT regressor search. This might be done to prune models that require long training times or to select only models that have desirable properties for the problem under consideration. Specifically, TPOT may be used to select the best pipelines it can find from the scikit-learn library combining 11 different regressors and 18 different preprocessing processes. This model selection process can done independently for each metabolite (Table 1). After TPOT determines the optimal models associated with each metabolite, the models are trained on the data set of interest and are ready for use to solve Eqs. (3) and (4). Models with the lowest tenfold cross-validated prediction root mean squared error may be selected. In this way, the best validated models are selected for use.

Figure 6:
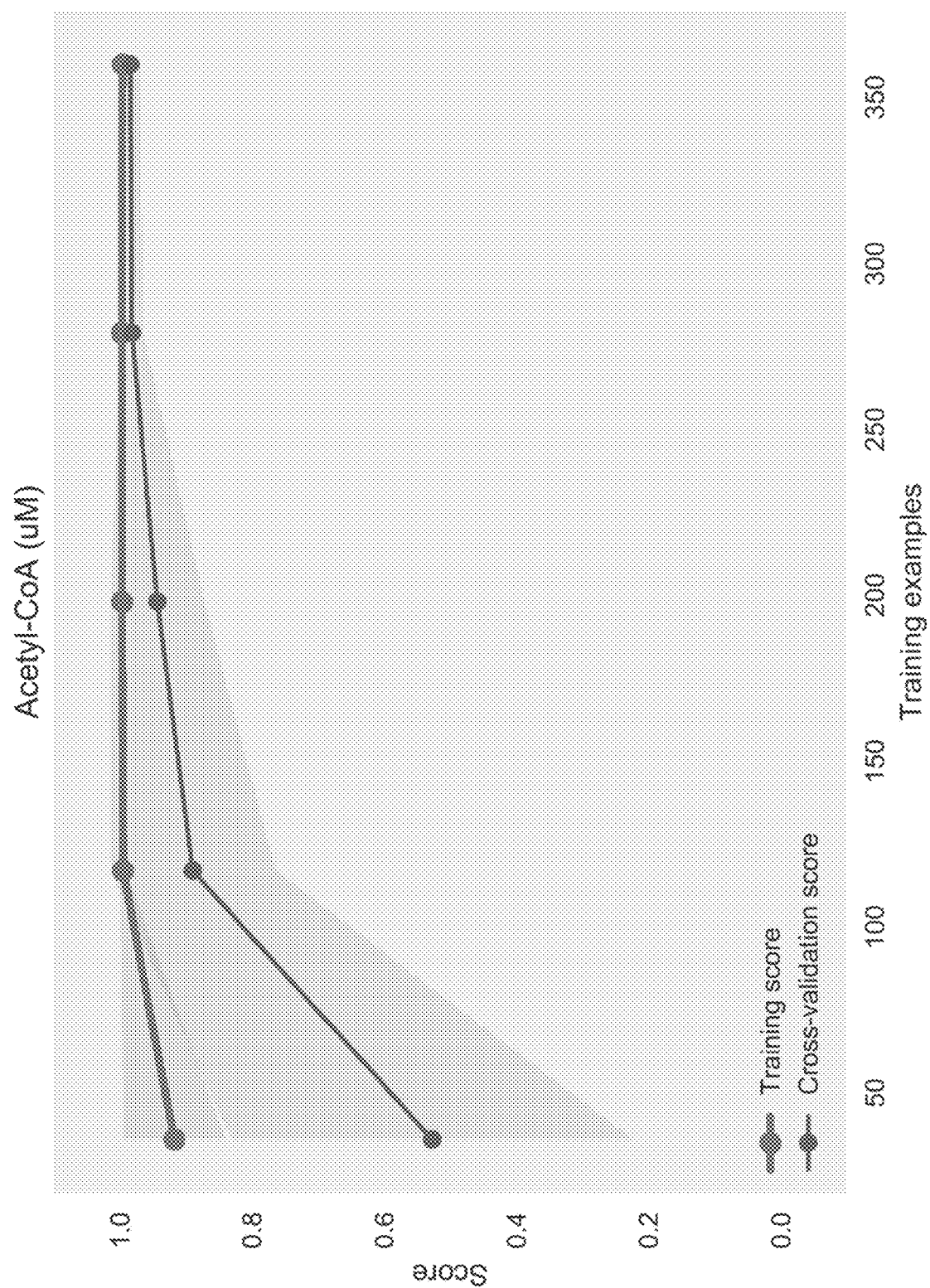
FIG. 6 is a plot showing cross validation and training scores as a function of training set size. This is a representative example of how model performance increased with the size of the data set provided. Cross validation techniques trained multiple models with a subset of the training data, and then test these model on data not used for training. In this case the training examples involved the time points for which derivatives were calculated from the training data, and proteomics and metabolomics data were available. In the training set each time series contained seven data points. These were too sparse to formulate accurate models. To overcome this a data augmentation scheme was employed where seven time points from the original data were expanded into 200 for each strain. This was done by filtering the data and interpolating over the filtered curve. In the plot, two data augmented strains were used where 360 points were used in the training set and 40 points were used in the test set.

After automated model selection via TPOT, each model may be evaluated based on its accuracy in predicting metabolite derivatives given protein and metabolite concentration at a given time point (FIG. 3). Each data set used for model fitting can be split into training and test sets ten times using the shuffle split methodology implemented in scikit-learn. After the model is fit, predictions on both the training and test sets may be computed for each metabolite model and their predictive ability quantified through a Pearson $R^2$ coefficient (e.g., FIG. 6).

Using the model. Once the models are trained, they can be used to predict metabolite concentrations by solving the following initial value problem using the same function $f$ learned in Eqs. (1) and (2):

$$\dot{m} = \tilde{f}(m, \tilde{p}) \quad (3)$$

$$m(t_0) = \tilde{m}(t_0) \quad (4)$$

This problem can be solved by integrating the system forward in time numerically. As a general purpose numerical integrator, a Runga Kutta 45 implementation may be used.

Data Set Curation and Synthesis

A number of different data sets may be used. The first may be an experimental data set curated from a previous publication, comprising three proteomic and metabolomic time-series (strains) from an isopentenol producing *E. coli* and three time-series (strains) from limonene producing *E. coli*. The second data set may involve computationally simulated data from a kinetic model of the limonene pathway, which may be used to test how the method performance scales with the number of time series used.

Description of a real time-series multiomics data set. Proteomics and metabolomics data for two different heterologous pathways engineered into an organism, such as the bacterium *E. coli*, may be obtained. There may be three (high, medium, and low production) variants for strains which produce isopentenol and limonene, respectively. All strains may be derived from *E. coli* DH1. The low and high-producing strain for each pathway may be used to predict the medium production strain dynamics by solving Eqs. (3) and (4).

Figure 4:
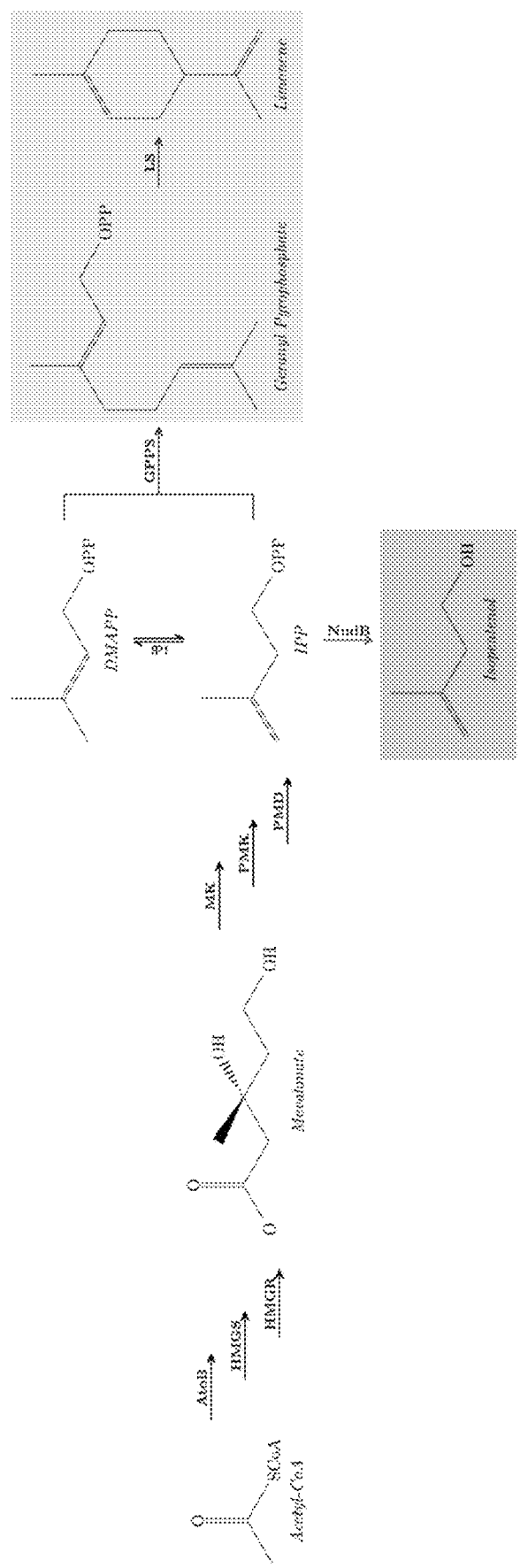
FIG. 4 shows a schematic illustration of limonene and isopentenol metabolic pathways. The machine learning method was tested on the limonene and isopentenol metabolic pathways. The limonene and isopentenol production pathways are variants of the mevalonate pathway. Time-series proteomics and metabolomics data were used to learn the dynamics of both the isopentenol and limonene producing strains. Additionally, a kinetic model was created and compared to the machine learning approach for the more complex limonene production pathway (FIG. 7). This pathway model was also used to generate simulated data to further evaluate the scaling properties of the proposed machine learning method.

The isopentenol producing strains (I1, I2 and I3) may be engineered to contain all of the proteins required to produce isopentenol from acetyl-CoA as (FIG. 4). I1 may be the unoptimized strain containing the naive variants of each protein in the pathway. I2 may differ from the base strain I1 in that it contained a codon optimized HMGR enzyme along with the positions of PMK and MK swapped on its operon. I3 may use a homolog, such as an HMGR homolog from *Staphylococcus aureus*.

Limonene producing strains (L1, L2, and L3) may produce limonene from acetyl-CoA (FIG. 4). L1 may be the un-optimized strain with the naively chosen variants for each protein in the pathway. It may have a two plasmid system where the lower and upper parts of the pathway are split between both constructs. L2 may be a DH1 variant that contains the entire limonene pathway on a single plasmid. L3 may be another two-plasmid strain where the entire pathway is present on the first plasmid, and the terpene synthases are on a second plasmid for increased expression. Starting at induction, each strain may have measurements taken at seven time points during fermentation over 72 hours. At each time point pathway, metabolite measurements and pathway protein measurements may be collected.

Data augmentation through filtering and interpolation. In the training set each time series may contain a number of data points, such as seven data points. These may be too sparse to formulate accurate models. To overcome this a data augmentation scheme may be employed where seven time points from the original data are expanded into 200 for each strain. This may be done by smoothing the data with a Savitzky-Golay filter and interpolating over the filtered curve (FIG. 2 and FIG. 5). When predicting the dynamics of a medium production strain from high and low producing strains, model selection may be performed by scoring each model using tenfold cross validation and a Pearson $R^2$ metric on two data augmented training strains.

Development of realistic kinetic models. To study the scaling of performance as more training sets are added, a realistic and dynamically complex model of the mevalonate pathway may be developed from known interactions extracted from the literature (FIGS. 4 and 7). The dynamic model may be implemented with Michaelis-Menten like kinetics and may be a 10-state coupled nonlinear system. Exemplary details of this kinetic model are described below. The objective may be to create a realistic model, relevant to metabolic engineering, for which learning the system dynamics is a non-trivial task on par with the difficulty of learning real system dynamics from experimental data.

Generation of a simulated data set. The kinetic model described above may be used to create a set of virtual data time-series (strains). The kinetic model coefficients may be chosen to be close to values available, such as values reported in the literature, while maintaining a non-trivial dynamic behavior.

A virtual strain may be created by first generating a pathway proteomic time series. This may be done by randomly choosing three coefficients for each protein ($k_f$, $k_m$, $k_l$), which specify a leaky hill function. The hill function may be used because it models the dynamics of protein expression from RNA accurately. This leaky hill function specifies the protein measurements for each time point and is defined in the eq. (5) below:

$$\hat{p}(t) = \frac{k_f t}{k_m + t} + k_l \qquad (5)$$

Once all protein time series are specified, they may be used in conjunction with the kinetic coefficients to solve the initial value problem in Eqs. (3) and (4) in order to determine the time series of metabolite concentrations. The resulting data set may be a collection of time-series measurements of different strain proteomics and metabolomics. All or some strains may use the same kinetic parameters and differential equations to generate the metabolomics measurements.

Fitting the Michaelis-Menten Kinetic Model

To compare the handcrafted kinetic model with the data-centric machine learning methodology, the parameters of the kinetic model may be fitted to strain data. To find the best fit, a differential evolution algorithm or process implemented in scipy may be used. This global optimizer may be chosen because its convergence is independent of the initial population choice and it tends to need less parameter tuning than other methods. All kinetic parameters may be constrained to be between $10^{-12}$ and $10^9$, for example. This large range of acceptable parameter values may allow for maximum flexibility of the kinetic model to describe the data.

Evaluation of Model Performance for Time Series

Dynamical prediction may be tested on a held back strain that is not used to train the model. When using the experimental data sets, the medium titer strains may be held back for testing. When using simulated data, a random strain from the data set may be selected. For each time series, agreement between predictions and test data may be assessed by calculating the root mean squared error (RMSE) of the predicted trajectories:

$$RMSE = \sqrt{\frac{1}{n}\sum_{j=1}^{n} \int_{t_0}^{t_f} (\overline{m}_j(t) - m_j(t))^2 \, dt}, \qquad (6)$$

where $\overline{m}_j(t)$ is the interpolation of the actual metabolite concentration of metabolite j at time t (FIG. 5), and $m_j(t)$ is the prediction obtained from solving Eqs. (3) and (4).

Example Learning Process and Strain Creation

Many machine learning techniques can be used to solve supervised learning problems. The techniques may use computational models trained to predict dependent variables from independent variables. A real valued dependent variable vector of protein and metabolite concentrations at a particular time point can be related to the derivatives of metabolite concentrations at the same time point. Learning these derivatives at a particular system state of a biological system can be equivalent to learning the dynamics of the entire biological system. Learning these derivatives can be possible because the independent variables contained sufficient information to predict dependent variables.

FIG. 2 shows a schematic illustration of a process 200 for learning metabolic pathway dynamics from time series proteomics and metabolomics data (or multiomics data general). In a cyclic fashion, cellular dynamics can be learned and used for mechanistic understanding or metabolic engineering. At block 204, time series experimental data (e.g., proteomics and metabolomics data) can be generated or acquired for several strains of an organism of interest.

At block 208, the time-series data traces can be smoothed and differentiated. Because the time-series data can be subject to measurement noise, estimating the derivatives carefully can be important. For example, a filter (e.g., a Savitzky-Golay filter) can be first applied to the noisy time-series data to find a smooth estimate of the data. This smooth function estimate can then be used to compute a more accurate estimate of the derivative. Once both the independent and dependent variable pairs have been created for training, a machine learning process can be applied to find the vector field which describes the metabolic system dynamics. The machine learning method can be a regressor, such as a random forest regressor. The regressor can be a metabolic engineering-specific, supervised learning regressor that restricts the function search space to the set of possible kinetic models. The derivatives help to provide examples of the dynamics at the states explored by each strain.

At block 212, the state-derivative pairs can be fed into a supervised learning method, such as a random forest regression method, to determine a metabolic pathway dynamic model representing the metabolic system dynamics of the organism. In one embodiment, the state can be represented by a protein concentration and a metabolite concentration. The machine learning method can be used to learn and generalize the metabolic system dynamics from the state-derivative pairs of each strain. For example, the data can be used to learn the relationships between each state and the corresponding derivative. Each unique strain can be modeled to have a unique proteomics profile, and the time-series proteomics data can be unique for each strain. At block 216, the model can then be used to simulate virtual strains and explore the metabolic space looking for mechanistic insight or commercially valuable designs. This process can then be repeated using the model to create new strains, which can further improve the accuracy of the dynamic model.

Each pathway dynamic model used to create simulated training data included free parameters which represent pathway kinetics, and exogenous variables which allow virtual strains to be expressed. Each unique strain was modeled to have a unique proteomics profile, and the time-series proteomics data was unique for each strain. When generating data, a realistic set of kinetic parameters for the pathway was randomly generated. Then a time-series data set corresponding to each virtual strain was generated. For training purposes, as many as 10,000 strains were generated at a time. As a result the data set was a collection of time-series of different strain proteomics and metabolomics data for a pathway with shared kinetic parameters.

The models learned can be useful for metabolic engineering. Having a predictive model of the dynamics of a metabolic network can allow rational engineering of strains for various objectives. Metabolic engineering can include maximizing titer or yield of a valuable biochemical. A dynamical model can be queried for strains which improve on existing design goals. In one embodiment, the method 200 can include designing a strain of the organism that corresponds to one of the strains simulated. The method 200 can include creating a strain of the organism corresponding to the simulated strain. The simulated strain can have one or more desired characteristics of the strain, such as titer, rater, and yield of a product of the metabolic pathway represented the metabolic pathway dynamic model. The method 200 may include receiving time-series proteomics and metabolomics data of the created strain. The model may be retrained using the time-series proteomics and metabolomics data of the created strain.

In one embodiment, a method 200 for simulating the metabolic pathway dynamics of a strain of an organism comprises: receiving time-series multiomics data comprising a first time-series multiomics data associated a metabolic pathway and a second time-series multiomics data associated with the metabolic pathway at block 204; determining derivatives of the first time-series multiomics data at block 208; training a machine learning model, representing a metabolic pathway dynamics model, using the first time-series multiomics data, the derivatives of the first time-series multiomics data, and the second time-series multiomics data, wherein the metabolic pathway dynamics model relates the first time-series multiomics data and the second time-series multiomics data to the derivatives of the first time-series multiomics data at block 212; and simulating a virtual strain of the organism using the metabolic pathway dynamics model at block 216. The method 200 may include designing a strain of the organism corresponding to the simulated strain, and/or creating a strain of the organism corresponding to the simulated strain.

The first time-series multiomics data may include time-series metabolomics data of a plurality of strains of an organism, and the time-series metabolomics data may include two or more time-series of a strain. The second time-series multiomics data may include time-series proteomics data of a plurality of strains of an organism, and the time-series proteomics data may include a plurality of time-series of a strain. The first time-series multiomics data may be, or include, time-series multiomics data of a plurality of strains of an organism, and wherein the first time-series multiomics data comprises time-series multiomics data of a plurality of strains of a different organism. The first time-series multiomics data or the second time-series multiomics data may be, or include, time-series proteomics data, time-series metabolomics data, time-series transcriptomics data, or a combination thereof. The first time-series multiomics data or the second time-series multiomics data may be associated with an enzymatic characteristic selected from the group consisting of a $k_{cat}$ constant, a $K_m$ constant, and a kinetic characteristics curve. The first time-series multiomics data and the second time-series multiomics data may include observations at corresponding time points.

The machine learning model may include a supervised machine learning model. The metabolic pathway dynamics model may include observable and unobservable parameters representing kinetics of the metabolic pathway. Training the machine learning model may include training the machine learning model using training data comprising an n-tuples of a first observation at a time point in the first time-series multiomics data, a second observation at the time point in the second time-series multiomics data, and a derivative of the first observation. Training the machine learning model may include selecting the machine learning model from a plurality of machine learning models using a tree-based pipeline optimization tool. Simulating the virtual strain of the organism may include integrating derivatives of the first time-series multiomics data outputted by the metabolic pathway dynamics model. Simulating a virtual strain of the organism using the metabolic pathway dynamics model may include simulating a virtual strain using the metabolic pathway dynamics model to change one or more of titer, rate, and yield of a product of a metabolic pathway represented by the metabolic pathway dynamics.

Development of a Kinetic Model for Limonene Synthesis

Below is an exemplary description of each reaction in the limonene pathway including likely inhibiting metabolites.

The descriptions provide a solid starting point for a mechanistic metabolic model for limonene production.

Reaction 1

Acetyl-CoA is converted to acetoacetyl-CoA using acetyl-CoA acetyltransferase (AtoB) using a ping-pong mechanism. This enzyme is inhibited by:

$$2\text{acetyl-CoA} \xrightarrow{AtoB} \text{CoA} + \text{acetoacetyl-CoA}.$$

The ping pong mechanism of this reaction is illustrated as:

The mass action law describing this mechanism of reaction 1 (R1) may be described by the following system of ordinary differential equations.

$$R_1 \begin{cases} \dot{s} = k_{r1}c + k_{r2}c^* - k_{f1}se - k_{f2}se^* \\ \dot{e} = k_{r1}c + k_{c2}c^* - k_{f1}se \\ \dot{c} = k_{f1}se - k_{r1}c - k_{c1}c \\ \dot{p}_1 = k_{c1}c \\ \dot{e}^* = k_{c1}c + k_{r2}c^* - k_{f2}se^* \\ \dot{c}^* = k_{f2}se^* - k_{r2}c^* - k_{c2}c^* \\ \dot{p}_2 = k_{c2}c^* \end{cases}$$

Using the quasi-steady state assumption this can be rewritten in a Michaelis-Menten formulation. The resulting equation which describes the pathway product in terms of substrate concentrations is given by:

$$p_2 = \frac{K_1 e_0 s}{K_2 + K_3 s}$$

$$p_2 = \frac{K_1 e_0 s}{K_2 + K_3 s},$$

where $K_1 = k_{c1}k_{c2}k_{f1}k_{f2}$ $K_2 = k_{c1}k_{c2}k_{f2} + k_{c1}k_{f1}(k_{c2}+k_{r2}) + k_{c2}k_{f2}k_{r1}$ $K_3 = (k_{c1}+k_{c2})k_{f1}k_{f2}$ Reaction 2

Acetoacetyl-CoA is converted to HMG-CoA by HMGS using a three-step ping pong mechanism reaction involving an acylation, a condensation, and a hydrolysis. The reaction is given by:

$$\text{acetyl-CoA} + \text{acetoacetyl-CoA} + H_2O \xrightarrow{HMGS} \text{HMG-CoA} + \text{CoA}.$$

The three step ping pong mechanism is as shown below:

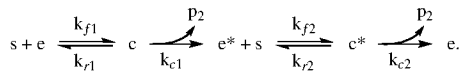

where $p_1$ is CoA and $p_2$ is HMG-CoA. The resulting differential equations for this system are given by:

$$R_2 \begin{cases} \dot{s}_1 = k_{r1}c - k_{f1}s_1 e \\ \dot{e} = k_{r1}c + k_{c2}s_3 c^* - k_{f1}s_1 e \\ \dot{c} = k_{f1}s_1 e - k_{r1}c - k_{c1}c \\ \dot{p}_1 = k_{c1}c \\ \dot{e}^* = k_{c1}c + k_{r2}c^* - k_{f2}s_2 e^* \\ \dot{s}_2 = k_{r2}c^* - k_{f2}s_2 e^* \\ \dot{c}^* = k_{f2}s_2 e^* - k_{c2}s_3 c^* - k_{r2}c^* \\ \dot{s}_3 = -k_{c2}s_3 c^* \\ \dot{p}_2 = k_{c2}c^* \end{cases}$$

Assuming quasi-steady state and constant $H_2O$ concentration yields the Michaelis-Menten Equations:

$$\dot{s}_1 = -\frac{K_1 e_0 s_1 s_2 s_3}{K_2 s_2 + K_3 s_1 + K_4 s_1 s_2}$$

$$\dot{s}_2 = -\frac{K_1 e_0 s_1 s_2 s_3}{K_2 s_2 + K_3 s_1 + K_4 s_1 s_2}$$

$$\dot{p}_2 = \frac{K_1 e_0 s_1 s_2}{K_2 s_1 + K_3 s_2 + K_4 s_1 s_2},$$

where $K_1 = k_{c1}k_{c2}k_{f1}k_{f2}$ $K_2 = k_{c1}k_{c2}k_{f2}s_3 + k_{c2}k_{f2}k_{r1}s_3$ $K_3 = k_{c1}k_{c2}k_{f1}s_3 + k_{c1}k_{f1}k_{r2}$ $K_4 = k_{c1}k_{f1}k_{f2} + k_{c2}k_{f1}k_{f2}s_3$ Reaction 3

Guessing an ordered sequential reaction mechanism with two competitive inhibitors with respect to HMG-CoA. This reaction is inhibited by acetyl-CoA and acetoacetyl-CoA. Because of similarity in substrate and inhibitor structure, it can assumed to be competitive with respect to HMG-CoA.

$$\text{HMG-CoA} + \text{NADPH} \xrightarrow{HMGR} \text{Mevalonate} + \text{NADP} + s_1 + e \underset{k_{r1}}{\overset{k_{f1}}{\rightleftharpoons}}$$

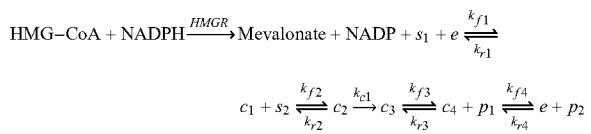

$$R_3 \begin{cases} \dot{s}_1 = k_{r1}c_1 - k_{f1}s_1 e \\ \dot{e} = k_{r1}c_1 - k_{f1}s_1 e + k_{f4}c_4 - k_{r4}p_2 e - k_{fi1}ei_1 - k_{fi2}ei_2 \\ \dot{c}_1 = k_{f1}s_1 e - k_{r1}c_1 - k_{f2}s_2 c_1 + k_{r2}c_2 \\ \dot{s}_2 = k_{r2}c_2 - k_{f2}s_2 c_1 \\ \dot{c}_2 = k_{f2}s_2 c_1 - k_{r2}c_2 - k_{c1}c_2 \\ \dot{c}_3 = k_{c1}c_2 + k_{r3}p_1 c_4 - k_{f3}c_3 \\ \dot{c}_4 = k_{f3}c_3 - k_{r3}p_1 c_4 + k_{r4}p_2 e - k_{f4}c_4 \\ \dot{c}_5 = k_{fi1}ei_1 - k_{ri1}c_5 \\ \dot{c}_6 = k_{fi2}ei_2 - k_{ri2}c_6 \\ \dot{p}_1 = k_{f3}c_3 - k_{r3}p_1 c_4 \\ \dot{p}_2 = k_{f4}c_4 - k_{r4}p_2 e \\ \dot{i}_1 = -k_{fi1}ei_1 + k_{ri1}c_5 \\ \dot{i}_2 = -k_{fi2}ei_2 + k_{ri2}c_6 \end{cases}$$

Assuming a roughly constant ratio of NADPH to NADP+ and quasi-steady state enzyme balance we can write these equations more simply as:

$$\dot{s}_1 = -\frac{K_1 e_0 s}{K_2 i_1 + K_3 i_2 + K_4 s + K_5}$$

$$\dot{p}_1 = \frac{K_1 e_0 s}{K_2 i_1 + K_3 i_2 + K_4 s + K_5}.$$

Reaction 4

Mevalonate kinase (MK) proceeds via an ordered sequential mechanism, where mevalonate binds to the enzyme first, followed by ATP. After catalysis, phosphomevalonate is released followed by ADP:

$$\text{ATP} + \text{mevalonate} \xrightarrow{MK} \text{CoA} + \text{phosphomevalonate}.$$

The ordered sequential mechanism for Mevalonate Kinase:

$$s_1 + e \underset{k_{r1}}{\overset{k_{f1}}{\rightleftharpoons}} c_1 + s_2 \underset{k_{r2}}{\overset{k_{f2}}{\rightleftharpoons}} c_2 \xrightarrow{k_{c1}} c_3 \underset{k_{r3}}{\overset{k_{f3}}{\rightleftharpoons}} c_4 + p_1 \underset{k_{r4}}{\overset{k_{f3}}{\rightleftharpoons}} e + p_2$$

$$R_4 \begin{cases} \dot{s}_1 = k_{r1}c_1 - k_{f1}s_1 e \\ \dot{e} = k_{r1}c_1 - k_{f1}s_1 e + k_{f4}c_4 - k_{r4}p_2 e \\ \dot{c}_1 = k_{f1}s_1 e - k_{r1}c_1 - k_{f2}s_2 c_1 + k_{r2}c_2 \\ \dot{s}_2 = k_{r2}c_2 - k_{f2}s_2 c_1 \\ \dot{c}_2 = k_{f2}s_2 c_1 - k_{r2}c_2 - k_{c1}c_2 \\ \dot{c}_3 = k_{c1}c_2 + k_{r3}p_1 c_4 - k_{f3}c_3 \\ \dot{c}_4 = k_{f3}c_3 - k_{r3}p_1 c_4 + k_{r4}p_2 e - k_{f4}c_4 \\ \dot{c}_5 = k_{fi1}ei_1 - k_{ri1}c_5 \\ \dot{c}_6 = k_{fi2}ei_2 - k_{ri2}c_6 \\ \dot{p}_1 = k_{f3}c_3 - k_{r3}p_1 c_4 \\ \dot{p}_2 = k_{f4}c_4 - k_{r4}p_2 e \\ \dot{i}_1 = -k_{fi1}ei_1 + k_{ri1}c_5 \\ \dot{i}_2 = -k_{fi2}ei_2 + k_{ri2}c_6 \end{cases}$$

GPP and FPP are both competitive inhibitors of MK with respect to ATP. In the *Streptococcus pneumoniae* homolog of mevalonate kinase, diphosphomevalonate (DPM) is an non-competitive inhibitor with respect to both substrates. DPM binds at an allosteric site, and inhibition cannot be overcome by an increasing substrate concentration.

The resulting Michaelis-Menten Equations Assuming ATP and ADP are roughly constant and two inhibitors:

$$\dot{s}_1 = -\frac{K_1 e_0 s}{K_2 i_1 + K_3 i_2 + K_4 s + K_5}$$

$$\dot{p}_1 = \frac{K_1 e_0 s}{K_2 i_1 + K_3 i_2 + K_4 s + K_5}.$$

Reaction 5

Phosphomevalonate Kinase proceeds with a random sequential bi-bi mechanism in the *S. Pneumoniae* homolog. The enzyme is kinetically characterized for *S. Cerevisiae*, however, it may be superior to use the better characterized enzyme in *S. Pneumoniae*.

$$\text{ATP} + \text{phosphomevalonate} \xrightarrow{PMK} \text{ADP} + \text{pyromevalonate}$$

$$s_1 + e \underset{k_{r1}}{\overset{k_{f1}}{\rightleftharpoons}} c_1 + s_2 \underset{k_{r2}}{\overset{k_{f2}}{\rightleftharpoons}} c_2 \xrightarrow{k_{c1}} c_3 \underset{k_{r3}}{\overset{k_{f3}}{\rightleftharpoons}} c_4 + p_1 \underset{k_{r4}}{\overset{k_{f4}}{\rightleftharpoons}} e + p_2$$

$$R_5 \begin{cases} \dot{s}_1 = k_{r1a}c_{1a} - k_{f1a}s_1 e + k_{r2b}c_2 - k_{f2b}s_1 c_{1b} \\ \dot{s}_2 = k_{r1b}c_{1b} - k_{f1b}s_2 e + k_{r2a}c_2 - k_{f2a}s_2 c_{1a} \\ \dot{e} = k_{r1a}c_{1a} + k_{r1b}c_{1b} - k_{f1b}s_2 e - k_{f1a}s_1 e + \\ \quad k_{f4a}c_{4a} + k_{f4b}c_{4b} - k_{r4a}p_2 e - k_{r4b}p_1 e \\ \dot{c}_{1a} = k_{f1a}s_1 e - k_{r1a}c_{1a} + k_{r2a}c_2 - k_{f2a}s_2 c_{1a} \\ \dot{c}_{1b} = k_{f1b}s_2 e - k_{r1b}c_{1b} + k_{r2b}c_2 - k_{f2b}s_1 c_{1b} \\ \dot{c}_2 = k_{f2a}s_2 c_{1a} - k_{r2a}c_2 + k_{f2b}s_1 c_{1b} - k_{r2b}c_2 - k_c c_2 \\ \dot{c}_3 = k_c c_2 + k_{r3a}c_{4a}p_1 - k_{f3a}c_3 + k_{r3b}c_{4b}p_2 - k_{f3b}c_3 \\ \dot{p}_1 = k_{f3a}c_3 - k_{r3a}c_{4a}p_1 + k_{f4b}c_{4b} - k_{r4b}p_1 e \\ \dot{p}_2 = k_{f3b}c_3 - k_{r3b}c_{4b}p_2 + k_{f4a}c_{4a} - k_{r4a}p_2 e \\ \dot{c}_{4a} = k_{f3a}c_3 - k_{r3a}c_{4a}p_1 + k_{f4a}c_{4a} - k_{r4a}p_2 e \\ \dot{c}_{4b} = k_{f3b}c_3 - k_{r3b}c_{4b}p_2 + k_{f4b}c_{4b} - k_{r4b}p_1 e \end{cases}$$

Briggs-Haldane Kinetics:

$$\dot{s} = -\frac{K_{cat} e_0 s}{K_d + s}$$

$$\dot{p} = \frac{K_{cat} e_0 s}{K_d + s},$$

where $$K_{cat} = k_{c1}$$

$$K_d = \frac{k_{c1} + k_{r1}}{k_{f1}}.$$

Reaction 6

PMD proceeds with an ordered sequential reaction mechanism. Ordered sequential mechanism with mevalonate 5-diphosphate as the first substrate to bind to the enzyme.

$$\text{diphosphomevalonate} + \text{ATP} \xrightarrow{PMD} \text{ADP} +$$
$$\text{phosphate} + \text{isopentenyl diphosphate} + CO_2$$

$$s_1 + e \underset{k_{r1}}{\overset{k_{f1}}{\rightleftharpoons}} c_1 + s_2 \underset{k_{r2}}{\overset{k_{f2}}{\rightleftharpoons}} c_2 \xrightarrow{k_{c1}} c_3 \underset{k_{r3}}{\overset{k_{f3}}{\rightleftharpoons}} c_4 +$$

$$p_1 \underset{k_{r4}}{\overset{k_{f4}}{\rightleftharpoons}} c_5 + p_2 \underset{k_{r5}}{\overset{k_{f5}}{\rightleftharpoons}} c_6 + p_3 \underset{k_{r6}}{\overset{k_{f6}}{\rightleftharpoons}} e + p_4$$

-continued $$R_6 \begin{cases} \dot{s}_1 = k_{r1}c_1 - k_{f1}s_1e \\ \dot{e} = k_{r1}c_1 - k_{f1}s_1e + k_{f6}c_6 - k_{r6}p_4e + \\ \quad k_{r i1a}c_{i1a} - k_{fi1a}i_1e + k_{r i1b}c_{i1b} - k_{fi1b}i_2e \\ \dot{c}_1 = k_{f1}s_1e - k_{r1}c_1 - k_{f2}s_2c_1 + k_{r2}c_2 + \\ \quad k_{r i2a}c_{i2a} - k_{fi2a}i_1c_1 + k_{r i2b}c_{i2b} - k_{fi2b}i_2c_1 \\ \dot{s}_2 = k_{r2}c_2 - k_{f2}s_2c_1 \\ \dot{c}_2 = k_{f2}s_2c_1 - k_{r2}c_2 - k_{c1}c_2 \\ \dot{c}_3 = k_{c1}c_2 + k_{r3}p_1c_4 - k_{f3}c_3 \\ \dot{p}_1 = k_{f3}c_3 - k_{r3}p_1c_4 \\ \dot{c}_4 = k_{f3}c_3 - k_{r3}p_1c_4 + k_{r4}p_2c_5 - k_{f4}c_4 \\ \dot{p}_2 = k_{f4}c_4 - k_{r4}p_2c_5 \\ \dot{c}_5 = k_{f4}c_4 - k_{r4}p_2c_5 - k_{f5}c_5 + k_{r5}c_6p_3 \\ \dot{p}_3 = k_{f5}c_4 - k_{r5}p_3c_6 \\ \dot{c}_6 = k_{f5}c_4 - k_{r5}p_3c_6 - k_{f6}c_6 + k_{r6}p_4e \\ \dot{p}_4 = k_{f6}c_6 - k_{r6}p_4e \\ \dot{c}_{i1a} = k_{fi1a}i_1e - k_{r i1a}c_{i1a} - k_{fia}s_1c_{i1a} + k_{rta}c_{i2a} \\ \dot{c}_{i1b} = k_{fi1b}i_2e - k_{r i1b}c_{i1b} - k_{ftb}s_1c_{i1b} + k_{rtb}c_{i2b} \\ \dot{c}_{i2a} = k_{fia}s_1c_{i1a} - k_{rta}c_{i2a} + k_{fi2a}i_1c_1 + k_{r i2a}c_{i2a} \\ \dot{c}_{i2b} = k_{ftb}s_1c_{i1b} - k_{rtb}c_{i2b} + k_{fi2b}i_2c_1 - k_{r i2b}c_{i2b} \\ \dot{i}_1 = k_{r i1a}c_{i1a} - k_{fi1a}i_1e + k_{r i2a}c_{i2a} - k_{fi2a}i_1c_1 \\ \dot{i}_2 = k_{r i1b}c_{i1b} - k_{fi1b}i_2e + k_{r i2b}c_{i2b} - k_{fi2b}i_2c_1 \end{cases}$$

Mixed Inhibition has been shown for mevalonate and phosphomevalonate with respect to ATP in the *Gallus gallus* homolog of the enzyme.

This may be actually competitive inhibition because dual mixed inhibition results in some nasty equations.

$$\dot{s}_1 = -\frac{K_1 e_0 s}{K_2 i_1 + K_3 i_2 + K_4 s + K_5}$$

$$\dot{p}_1 = \frac{K_1 e_0 s}{K_2 i_1 + K_3 i_2 + K_4 s + K_5}$$

Reaction 7

Isopentenyl diphosphate isomerase (IDI) mechanism with irreversible inhibition is shown below.

Isopentenyl diphosphate $\xrightarrow{IDI}$ Dimethylallyl diphosphate $$s + e \underset{k_{r1}}{\overset{k_{f1}}{\rightleftharpoons}} c \xrightarrow{k_{c1}} e + p$$

$$R_7 \begin{cases} \dot{s} = k_{r1}c - k_{f1}se \\ \dot{e} = k_{r1}c - k_{f1}se + k_{c1}c \\ \dot{c} = k_{f1}se - k_{r1}c = k_{c1}c \\ \dot{p}_1 = k_{c1}c \end{cases}$$

Briggs-Haldane Kinetics:

$$\dot{s} = -\frac{K_{cat} e_0 s}{K_d + s}$$

$$\dot{p} = \frac{K_{cat} e_0 s}{K_d + s},$$

where $$K_{cat} = k_{c1}$$

$$K_d = \frac{k_{c1} + k_{r1}}{k_{f1}}$$

Reaction 8

The geranyl diphosphate synthase (GPPS) mechanism is shown below.

dimethylallyl diphosphate + isopentenyl diphosphate $\xrightarrow{GPPS}$ diphosphate + geranyl diphosphate $$s_1 + e \underset{k_{r1}}{\overset{k_{f1}}{\rightleftharpoons}} c_1 + s_2 \underset{k_{r2}}{\overset{k_{f2}}{\rightleftharpoons}} c_2 \xrightarrow{k_{c1}} c_3 \underset{k_{r3}}{\overset{k_{f3}}{\rightleftharpoons}} c_4 + p_1 \underset{k_{r4}}{\overset{k_{f4}}{\rightleftharpoons}} c_5 + p_2$$

$$R_8 \begin{cases} \dot{s}_1 = k_{r1}c_1 - k_{f1}s_1e \\ \dot{e} = k_{r1}c_1 - k_{f1}s_1e + k_{f4}c_4 - k_{r4}p_2e \\ \dot{c}_1 = k_{f1}s_1e - k_{r1}c_1 - k_{f2}s_2c_1 + k_{r2}c_2 \\ \dot{s}_2 = k_{r2}c_2 - k_{f2}s_2c_1 \\ \dot{c}_2 = k_{f2}s_2c_1 - k_{r2}c_2 - k_{c1}c_2 \\ \dot{c}_3 = k_{c1}c_2 + k_{r3}p_1c_4 - k_{f3}c_3 \\ \dot{c}_4 = k_{f3}c_3 - k_{r3}p_1c_4 + k_{r4}p_2e - k_{f4}c_4 \\ \dot{p}_1 = k_{f3}c_3 - k_{r3}p_1c_4 \\ \dot{p}_2 = k_{f4}c_4 - k_{r4}p_2e \end{cases}$$

Briggs-Haldane Kinetics:

$$\dot{s}_1 = -\frac{K_1 e_0 s_1 s_2}{K_2 + K_3 s_1 K_4 s_2 + s_1 s_2}$$

$$\dot{s}_2 = -\frac{K_1 e_0 s_1 s_2}{K_2 + K_3 s_1 K_4 s_2 + s_1 s_2}$$

$$\dot{p} = \frac{K_1 e_0 s_1 s_2}{K_2 + K_3 s_1 K_4 s_2 + s_1 s_2}.$$

Reaction 9

Limonene Synthase finally makes limonene.

geranyl diphosphate $\xrightarrow{LS}$ limonene + diphosphate $$s + e \underset{k_{r1}}{\overset{k_{f1}}{\rightleftharpoons}} c_1 \xrightarrow{k_{c1}} c_2 \underset{k_{r2}}{\overset{k_{f2}}{\rightleftharpoons}} c_3 + p_1 \underset{k_{r3}}{\overset{k_{f3}}{\rightleftharpoons}} e + p_2$$

$$R_9 \begin{cases} \dot{s}_1 = k_{r1}c_1 - k_{f1}se \\ \dot{e} = k_{r1}c_1 - k_{f1}se + k_{f3}c_3 - k_{r3}p_2e \\ \dot{c}_1 = k_{f1}se - k_{r1}c_1 - k_{c1}c_1 \\ \dot{c}_2 = k_{r2}p_1c_3 - k_{f2}c_2 + k_{c1}c_1 \\ \dot{c}_3 = k_{f2}c_2 + k_{r3}p_2e - k_{f3}c_3 \\ \dot{p}_1 = k_{f2}c_3 - k_{r2}p_1c_3 \\ \dot{p}_2 = k_{f3}c_3 - k_{r3}p_2e \end{cases}$$

Briggs-Haldane Kinetics:

$$\dot{s} = -\frac{K_1 e_0 k_{f3} s}{K_1 s + K_2 p_2 + K_3 p_1 s + K_4 p_1 p_2 + K_5 p_1 p_2 + K_6 s + K_7}$$

$$\dot{p}_1 = \frac{\begin{array}{c} e_0 k_{f2}(K_1 s + K_2 p_2 - K_3 p_1 s - \\ K_4 p_1 p_2 - K_5 p_1 p_2) \end{array}}{K_1 s + K_2 p_2 + K_3 p_1 s + K_4 p_1 p_2 + K_5 p_1 p_2 + K_6 s + K_7}$$

$$\dot{p}_2 = \frac{K_1 e_0 k_{f3} s}{K_1 s + K_2 p_2 + K_3 p_1 s + K_4 p_1 p_2 + K_5 p_1 p_2 + K_6 s + K_7}$$

$$K_1 = k_{c1} k_{f1} k_{f2}$$

$$K_2 = k_{c1} k_{f2} k_{r3} + k_{f2} k_{r1} k_{r3}$$

$$K_3 = k_{c1} k_{f1} k_{r2}$$

-continued $K_4 = k_{c1}k_{r2}k_{r3}$ $K_5 = k_{r1}k_{r2}k_{r3}$ $K_6 = k_{c1}k_{f1}k_{f3} + k_{f1}k_{f2}k_{f3}$ $K_7 = k_{c1}k_{f2}k_{f3} + k_{f2}k_{f3}k_{r1}$.

Composite Model

Figure 8:
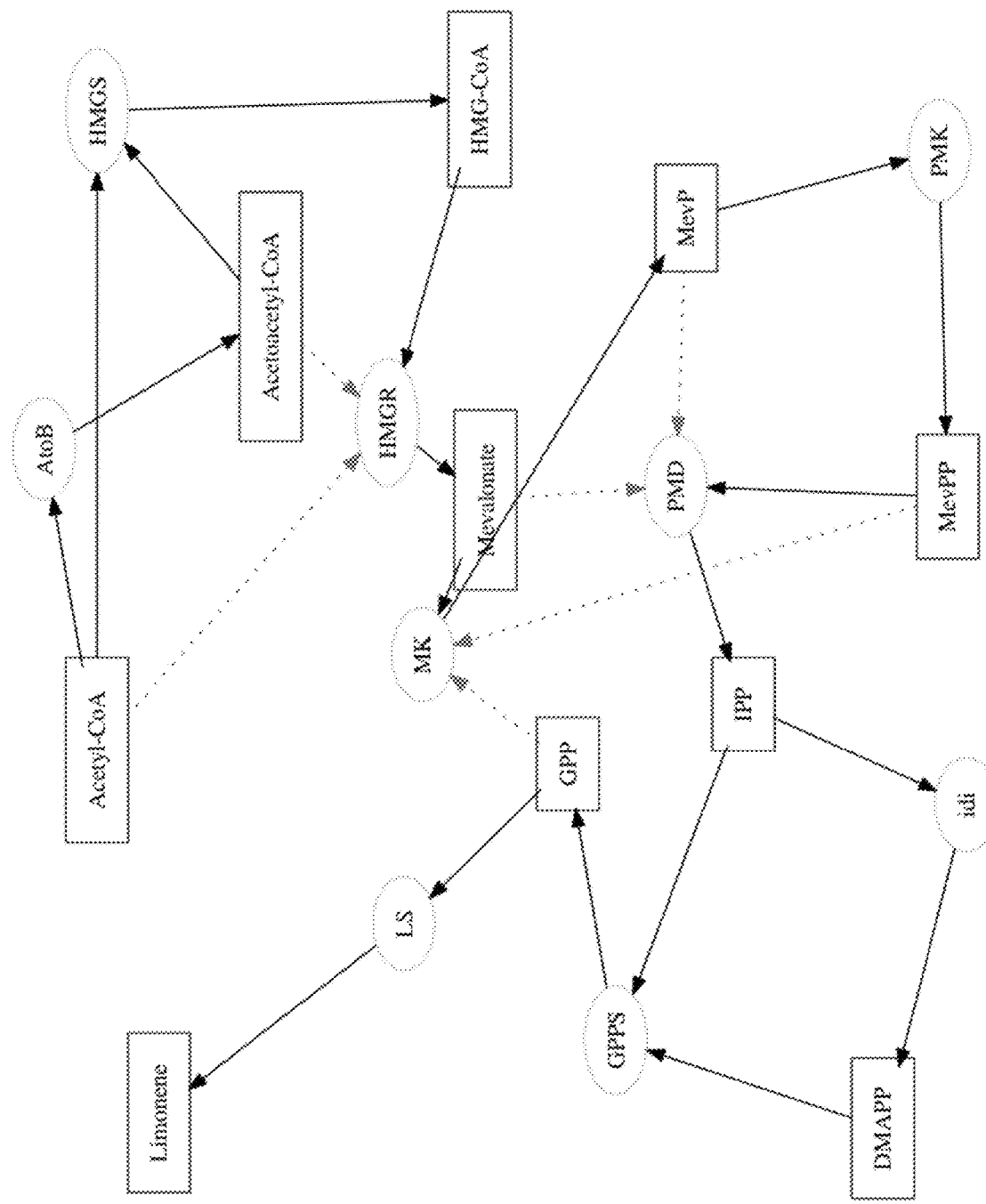
FIG. 8 is a schematic illustration showing a set of reactions and inhibition relationships. The metabolites are shown inside rectangles, the enzymes are shown inside circles, solid arrows indicate forward flow into the next component, and dashed arrows indicate an inhibition relationship between the two species.

The complete set of reactions and inhibition relationships are given shown in FIG. 8. The Metabolites are inside of rectangles, the enzymes are in circles. Solid arrows indicate forward flow into the next component. Dashed arrows indicate an inhibition relationship between the two species.

Reduced Order Michaelis-Menten Kinetics

Using the relationships derived above, a complete Michaelis-Menten description of the system is shown below.

$$\frac{d[A-\text{CoA}]}{dt} = \frac{K_{1,1}[AtoB][A-\text{CoA}]}{K_{1,2} + K_{1,3}[A-\text{CoA}]} -$$

$$\frac{K_{2,1}[\text{HMGS}][A-\text{CoA}][AA-\text{CoA}]k_{s3}}{K_{2,2}[AA-\text{CoA}] + K_{2,3}[A-\text{CoA}] + K_{2,4}[A-\text{CoA}][AA-\text{CoA}]}$$

$$\frac{d[AA-\text{CoA}]}{dt} = \frac{K_{1,1}[AtoB][A-\text{CoA}]}{K_{1,2}K_{1,3}[A-\text{CoA}]} -$$

$$\frac{K_{2,1}[\text{HMGS}][A-\text{CoA}][AA-\text{CoA}]k_{s3}}{K_{2,2}[AA-\text{CoA}] + K_{2,3}[A-\text{CoA}] + K_{2,4}[A-\text{CoA}][AA-\text{CoA}]}$$

$$\frac{d[\text{HMG-CoA}]}{dt} = \frac{K_{2,1}[\text{HMGS}][A-\text{CoA}][AA-\text{CoA}]k_{s3}}{K_{2,2}[A-\text{CoA}] + K_{2,3}[A-\text{CoA}] + K_{2,4}[A-\text{CoA}][AA-\text{CoA}]} -$$

$$\frac{K_{3,1}[\text{HMGR}][\text{HMG-CoA}]}{K_{3,2}[A-\text{CoA}] + K_{3,3}[AA-\text{CoA}] + K_{3,4}[\text{HMG-CoA}] + K_{3,5}}$$

$$\frac{d[Mev]}{dt} = \frac{K_{3,1}[\text{HMGR}][\text{HMG-CoA}]}{K_{3,2}[A-\text{CoA}] + K_{3,3}[AA-\text{CoA}] + K_{3,4}[\text{HMG-CoA}] + K_{3,5}} -$$

$$\frac{K_{4,1}[MK][Mev]}{K_{4,2}[GPP] + K_{4,3}[MevP] + K_{4,4}[Mev] + K_{4,5}}$$

$$\frac{d[MevP]}{dt} = \frac{K_{4,1}[MK][Mev]}{K_{4,2}[GPP] + K_{4,3}[MevP] + K_{4,4}[Mev] + K_{4,5}} -$$

$$\frac{K5,1[PMK][MevP]}{K_{5,1} + [MevP]}$$

$$\frac{d[MevPP]}{dt} = \frac{K5,1[PMK][MevP]}{K_{5,1} + [MevP]} -$$

$$\frac{K_{6,1}[PMD][MevPP]}{K_{6,2}[MevP] + K_{6,3}[Mev] + K_{6,4}[MevPP] + K_{6,5}}$$

$$\frac{d[IPP]}{dt} = \frac{K_{6,1}[PMD][MevPP]}{K_{6,2}[MevP] + K_{6,3}[Mev] + K_{6,4}[MevPP] + K_{6,5}} -$$

$$\frac{K_{7,1}[IDI][IPP]}{K_{7,2} + [IPP]} - \frac{K_{8,1}[GPPS][IPP][DMAPP]}{K_{8,2} + K_{8,3}[IPP]K_{8,4}[DMAPP] + [IPP][DMAPP]}$$

$$\frac{d[DMAPP]}{dt} = \frac{K_{7,1}[IDI][IPP]}{K_{7,2} + [IPP]} -$$

$$\frac{K_{8,1}[GPPS][IPP][DMAPP]}{K_{8,2} + K_{8,3}[IPP] + K_{8,4}[DMAPP] + [IPP][DMAPP]}$$

$$\frac{d[GPP]}{dt} = \frac{K_{8,1}[GPPS][IPP][DMAPP]}{K_{8,2} + K_{8,3}[IPP]K_{8,4}[DMAPP] + [IPP][DMAPP]} -$$

$$\frac{K_{9,1}[LS][GPP]}{K_{9,2} + [GPP]}$$

$$\frac{d[\text{Limonene}]}{dt} = \frac{K_{9,1}[LS][GPP]}{K_{9,2} + [GPP]}$$

Alternative Embodiments

In one embodiment, data on all relevant metabolites of interest is available. The system may have no unmeasured memory states. So, only data on the previous time point can be used to predict the next state. In one embodiment, models can be trained using partial knowledge of the state and a larger time series. Accordingly, fewer measurements may be used to accomplish the same dynamical estimation.

In one embodiment, the measurement of the entire state and its derivative at every time point can be noisy. These measurements may be difficult to acquire for the entire metabolism. In cases where the entire state cannot be measured, the methods disclosed herein can predict the derivatives of the measured quantities from a limited time history of the measurements taken. Modern deep learning techniques, such as long short term memory recurrent neural nets, can be implemented. The machine learning methods implemented can affect the number of strains for training effective models for modeling metabolic systems.

In one implementation, other supervised learning techniques may be used to improve predictions. For example, tree-based pipeline optimization tool (TPOT) may be used to combine, through genetic algorithms or processes, 11 different machine learning regressors and 18 different preprocessing (feature selection) methods. Additional supervised learning techniques may be included in this approach by adding them to the scikit-learn library. For example, TPOT may automatically test them and use them if they provide more accurate predictions than the techniques used here. Other methods for ML include deep-learning (DL) techniques based on neural networks. Data for training a DL-based model for learning and predicting metabolic pathway dynamics may be obtained. For example, data for more than 1000 strains may be obtained Mechanistic insights may be inferred from ML approaches disclosed herein. Exemplary possibilities for this inference include: (1) for any particular ML model that produces good fits, the most relevant features, such as protein x has the highest weight in determining y molecule concentration, provides a prioritized list of putative mechanistically linked parts that can be further investigated. (2) the ML model can be used as a surrogate for high-throughput experiments to derive mechanistic biological insights (FIG. 15). Another example of this approach involves studying toxicity by adding cell biomass (through optical density (OD)) to the measurements and simulate for a variety of scenarios (protein inputs) the correlation between OD and all metabolites: a negative correlation would signal putative toxic metabolites.

The methods can include incorporating prior knowledge into the ML approach. In one implementation, the method constrains the vector fields that are learned using any biological intuition. Biological facts may be known about these dynamical systems that could be used to improve the performance of the methods. For example, genome-scale stoichiometric constraints could provide guarantees that the resulting system dynamics conserve mass and conform to prior knowledge about the organism.

The ML-based methods of the disclosure may only require little prior biological knowledge and may be extended for use with different data inputs or other types of applications. For example, transcriptomics data may be used as input. Given the current exponential increase in sequencing capabilities, transcriptomics data may be more amenable to high-throughput production than proteomics and metabolomics data. Transcriptomics data correlate with proteomics, and the methods may require more time-series data for accurate predictions. As another example, the ML method may be used to predict proteomics in addition to metabolomics time series. The input and output of the ML method may include genome-scale multiomics data. The genome-scale multiomics data may be dense.

In one implementation, the predictive capabilities of the machine learning method of with respect to the Michaelis-Menten approach proceed, in part, from indirectly accounting for host metabolism effects through proxies, such as metabolites or proteins that are affected indirectly by host metabolism. Hence, more comprehensive metabolomics and proteomics (as well as transcriptomics) data sets may increase the method predictive accuracy. The methods may be used to predict microbial community dynamics, as compared to intracellular pathway prediction, using meta-proteomics and metabolite concentration data as inputs.

Execution Environment

Figure 9:
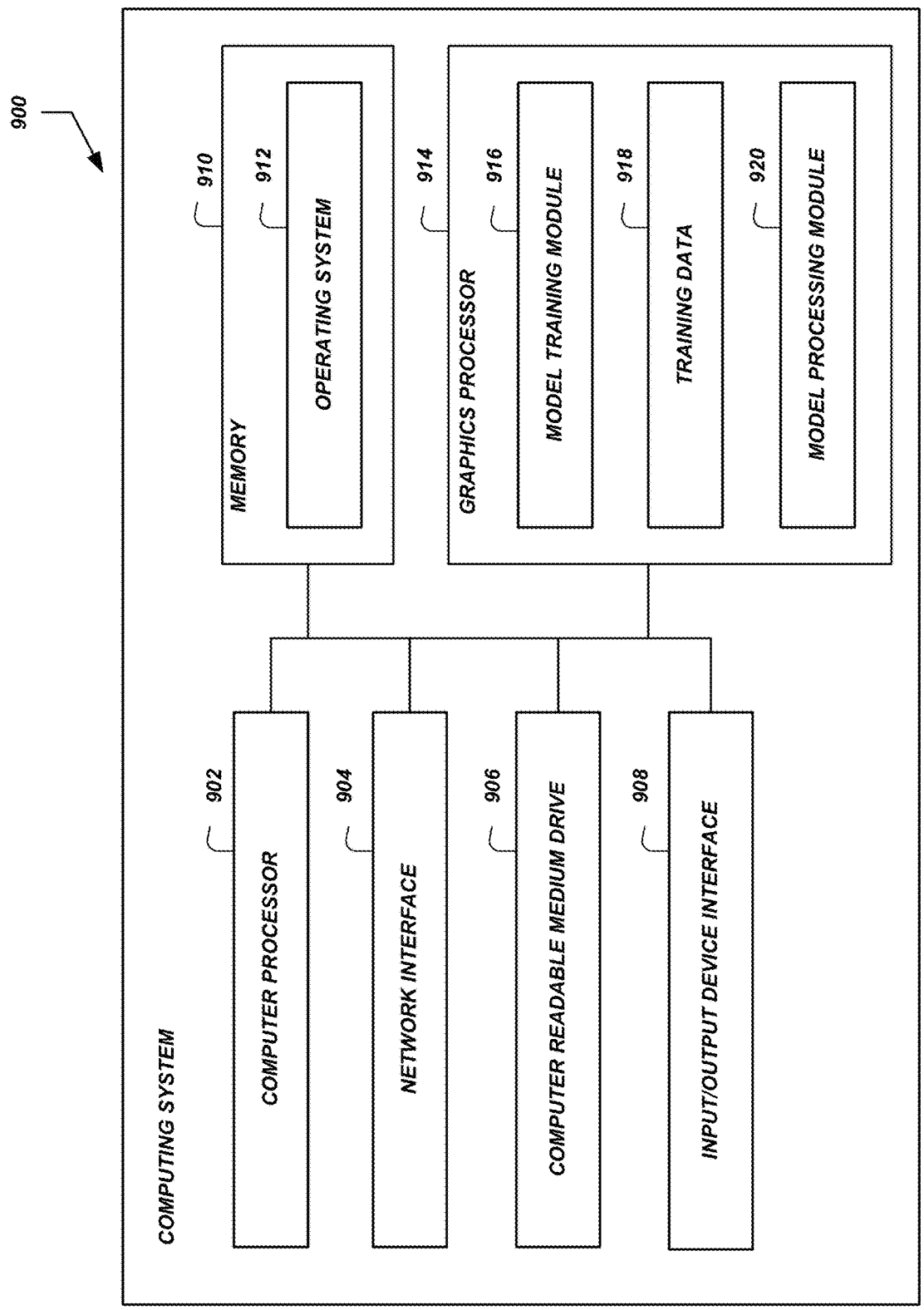
FIG. 9 is a block diagram of an illustrative computing system configured to implement training and processing of a machine learning model according to some embodiments.

FIG. 9 illustrates an example computing system 900 that may be used in some embodiments to execute the processes and implement the features described herein. In some embodiments, the computing system 900 may include: one or more computer processors 902, such as physical central processing units ("CPUs"); one or more network interfaces 904, such as a network interface cards ("NICs"); one or more computer readable medium drives 906, such as high density disks ("HDDs"), solid state drives ("SDDs"), flash drives, and/or other persistent non-transitory computer-readable media; an input/output device interface 908, such as an IO interface in communication with one or more microphones; one or more computer readable memories 910, such as random access memory ("RAM") and/or other volatile non-transitory computer-readable media; and one or more graphical processors 914, such as graphics processing units ("GPUs").

The network interface 904 can provide connectivity to one or more networks or computing systems. The computer processor 902 can receive information and instructions from other computing systems or services via the network interface 904. The network interface 904 can also store data directly to the computer-readable memory 910. The computer processor 902 can communicate to and from the computer-readable memory 910, execute instructions and process data in the computer readable memory 910, etc.

The computer readable memory 910 may include computer program instructions that the computer processor 902 executes in order to implement one or more embodiments. The computer readable memory 910 can store an operating system 912 that provides computer program instructions for use by the computer processor 902 in the general administration and operation of the computing system 900. The computer readable memory 910 can further include computer program instructions and other information for implementing aspects of the present disclosure.

In some embodiments, the graphics processor 914 can include graphics memory such as random access memory ("RAM"). The graphics memory may include a NN and/or computer program instructions that the graphics processor 914 executes in order to implement one or more embodiments. For example, in one embodiment, the graphics memory may include a machine learning model training module 916 that performs the process 200 and/or 300 described above (or portions thereof) to obtain, generate, or otherwise process training data 918, train a machine learning model with the obtained, generated, or otherwise processed training data, and use the trained machine learning model for determining recommendations for users. In some embodiments, the training data 918 currently being processed by the NN may also be stored in the graphics memory, while the remainder of the training data can be stored in some other location, such as memory 910, a computer-readable medium drive 906, a network-accessible data store, etc. As another example, the graphics memory may include a machine learning model processing module 920 that performs portions of the methods described herein to process the machine learning model generated by, for example, the machine learning model training module 916. In some implementations, the computing system 900 can include both the machine learning model training module 916 and the machine learning model processing module 920. In some implementations, the computing system 900 can include one of the machine learning model training module 916 or the machine learning model processing module 920. In some embodiments, multiple computing systems 900 may communicate with each other via their respective network interfaces 904, and can implement machine learning model training or processing separately (e.g., each computing system 900 may execute one or more separate instances of the processes 200 and/or 300), in parallel (e.g., each computing system 900 may execute a portion of a single instance of a process 200 and/or 300), etc.

EXAMPLE

Some aspects of the embodiments discussed above are disclosed in further detail in the following example, which are not in any way intended to limit the scope of the present disclosure.

Example 1

Determining Kinetic Models Using Meta Learning

This example demonstrates determining kinetic models using meta learning from time-series data using formulation I above.

The supervised learning method described above (FIGS. 1 and 2, Eqs. (1), (2), (3) and (4)) under Formulation I were used to predict pathway dynamics (i.e., metabolite concentrations as a function of time) from protein concentration data for two pathways of relevance to metabolic engineering and synthetic biology: a limonene producing pathway and an isopentenol producing pathway (FIG. 4). For each pathway, experimental times-series data obtained from the low and high biofuel producing strains were used as training data sets for a ML model, which was the used to predict the dynamics for the medium producing strains. TPOT was used to select the best pipelines it can find from the scikit-learn library combining 11 different regressors and 18 different preprocessing methods. This model selection process was done independently for each metabolite (Table 1). After TPOT determines the optimal models associated with each metabolite, the models were trained on the data set of interest and are ready for use to solve Eqs. (3) and (4). Models with the lowest tenfold cross-validated prediction root mean squared error was selected. In this way, the best validated models were selected for use. Because of the paucity of dense multiomics time-series data sets, simulated data sets were used (FIG. 7) to study the algorithm's performance as more training data sets (strains) were added.

TABLE 1

Table containing which machine learning model pipeline was used for each metabolite derivative prediction along with a measure of each models' performance.

| Pathway | Metabolite | Machine Learning Model | Fit Quality (R Value) |
|---|---|---|---|
| Experimental Isopentenol | Acetyl-CoA | Extra Trees Regressor with Polynomial Features | 1.000 |
| | HMG-CoA | Lasso Lars CV<br>→Min Max Sealer<br>→Gradient Boosting Regressor<br>→Decision Tree Regressor | 0.993 |
| | Mevalonate | Extra Trees Regressor | 1.000 |
| | Mev-P | FastICA<br>→LinearSVR<br>→Extra Trees Regressor | 1.000 |
| | IPP/DMAPP | Extra Trees Regressor | 1.000 |
| | Isopentenol | RidgeCV<br>→Extra Trees Regressor | 1.000 |
| Experimental Limonene | Acetyl-CoA | FastICA<br>→Polynomial Features<br>→Decision Tree Regressor<br>→FastICS<br>→Lasso-LarsCV | 0.996 |
| | HMG-CoA | FastICA<br>→One Hot Encoder<br>→Polynomial Features<br>→Max Abs Scaler<br>→K-Neighbors Regressor | 0.944 |
| | Mevalonate | Variance Threshold<br>→ RidgeCV<br>→Min Max Scaler<br>→K-Neighbors Regressor | 1.000 |
| | Mev-P | Extra Trees Regressor<br>→Random Forest Regressor<br>→Extra Trees Regressor<br>→Decision Tree Regressor | 0.994 |
| | IPP/DMAPP | Max Abs Scaler<br>→PCA<br>→Max Abs Scaler<br>→Max Abs Scaler<br>→ FastICA<br>→Max Abs Scaler<br>→RBFSampler<br>→ LassoLarsCV | 0.986 |
| | Limonene | Extra Trees Regressor<br>→ Random Forest Regressor | 1.000 |
| Simulated Limonene | Acetyl-CoA | Random Forest Regressor with Polynomial Features | 0.994 |
| | Acetoacetyl-CoA | Random Forest Regressor | 0.997 |
| | HMG-CoA | Extra Trees Regressor | 1.000 |
| | Mevalonate | Extra Trees Regressor | 0.998 |
| | Mev-P | Min-Max Scaler<br>→Robust Scaler<br>→Extra Trees Regressor | 0.997 |
| | Mev-PP | PCA<br>→ Extra Trees Regressor | 1.000 |
| | IPP | Extra Trees Regressor | 0.997 |
| | DMAPP | Extra Trees Regressor<br>→ LassoLarsCV | 1.000 |
| | GPP | Fast ICA<br>→K-Neighbors Regressor | 1.000 |
| | Limonene | K-Neighbors Regressor | 0.996 |

Qualitative Predictions of Limonene and Isopentenol Pathway Dynamics were Obtained with Two Time-Series Observations Two time-series (strains) were enough to train the ML model to produce acceptable predictions for most metabolites. The predictions of derivatives from proteomics and metabolomics were quite accurate (aggregate Pearson R value of 0.973), any small error in these predictions may compound quickly when solving the initial value problem given by Eqs. (3) and (4). For example, predictions for a given time point depend on the accuracy of all previous time points. The method produced respectable qualitative and quantitative predictions of metabolite concentrations for a strain it had never seen before (FIGS. 10A-10F and 11A-11F). For some metabolites (33%), the predictions were quantitatively close to the measured profile: acetyl-CoA (83.4% error, FIG. 10A) and isopentenol (43.7% error, FIG. 10F) for the isopentenol producing pathway; Acetyl-CoA (128.2% error, FIG. 11A), HMG-CoA (83.9% error, FIG. 11B) and limonene (82.9% error, FIG. 11F) for the limonene producing pathway. For most metabolites (42%), the predictions were off by a scale factor, but they were able to qualitatively reproduce the metabolite behavior. For example, for mevalonate in the isopentenol producing pathway (FIG. 10C) and mevalonate in the limonene producing pathway (FIG. 11C) the predictions reproduce the initial increase of metabolite concentration followed by a saturation. For IPP/DMAPP (FIG. 10E) or mevalonate phosphate (FIG. 10D) in the isopentenol pathway, the prediction reproduced qualitatively the concentration increase, followed by a peak and a decrease. The prediction of even just this type of qualitative behavior may be useful to metabolic engineers in order to obtain an intuitive understanding of the pathway dynamics and design better versions of it. By simulating several scenarios the metabolic engineer can extract qualitative knowledge (such as metabolite x seems toxic, or protein y seems regulated by metabolite x) that can lead to testable hypotheses. Finally, in a minority of cases (25%), the predictions required improvements both quantitatively and qualitatively: such as HMG-CoA for the isopentenol producing pathway (FIG. 10B), Mevalonate phosphate (FIG. 11D), and IPP/DMAPP (FIG. 11E) for the limonene producing pathway. The predictions for both final products (limonene and isopentenol) fell in the group of quantitatively accurate predictions. This may be important because, for the purpose of guiding metabolic engineering, it is the final product predictions that are relevant.

The machine learning approach outperformed a handcrafted kinetic model of the limonene pathway (FIGS. 11A-11F). A realistic kinetic model of this pathway was built and fit to the data, leaving all kinetic constants as free parameters (FIGS. 4 and 7). The kinetic model notably failed to capture the qualitative dynamics for Acetyl-CoA, HMG-CoA, mevalonate, and IPP/DMAPP (FIGS. 11A-11C, 11E). More quantitatively, the machine learning model produced an average 130% error (RMSE=8.42) vs. an average 144% (RMSE=10.04) for the kinetic model. Hence, even a machine learning model informed by the time-series data of just two strains was able to outperform the handcrafted kinetic model, which required domain expertise and significant time investment to construct. The machine learning approach, however, is more easily generalizable, and it can be reapplied for a new pathway, host or product by feeding it the corresponding data. Once the predictions were made for the limonene pathway, results for the isopentenol pathway can be obtained just by changing the time-series data input. In contrast, in order to make predictions for the isopentenol pathway a new kinetic model would have to be built. Kinetic models become more difficult to construct as the size of the reaction network increases and as the knowledge of the relevant network decreases. Additionally, all kinetic relationships must be known or inferred, whereas unknown relationships can be uncovered from data using a machine learning approach. The machine learning approach only requires a sufficient amount of data to disentangle these relationships.

The model was able to perform well even though the training sets corresponded to pathways which differed in more than just protein levels. This may be useful because the model was designed to take protein concentrations as input (FIG. 1) in order to predict pathway dynamics, assuming the rest of pathway characteristics to remain the same. The method can be applied to solve a wide range of metabolic engineering needs. For example, the model can be applied to promoters and ribosome-binding sites (RBSs) being modified in order to affect the resulting protein concentrations. As another example, the model can aid in designing metabolic engineering strategies, such as changing a given enzyme in order to access faster or slower catalytic rates (i.e., $k_{cat}$). The model was able to provide good predictions for I3, which used a HMGR analog form *Staphylococcus aureus*, and I2, which used a codon optimized HMGR. Without being limited by theories, $k_{cat}$ changes may be renormalized into (and be equivalent to) protein abundance changes. In one implementation, this method may be expanded to include enzyme characteristics as input (besides the proteomics data): $k_{cat}$ and $K_m$ constants or even full kinetic characterization curves.

Increasing the Number of Strains Improves the Accuracy of Dynamic Predictions

Simulated data was used to show that predictions improved markedly as more data sets are used for training. Simulated data sets had the advantage of providing unlimited samples to thoroughly test scaling behavior, and allowed a wider variety of types of dynamics than experimentally accessible to be explored. Moreover, the dense multiomics time-series data sets needed as training data may be rare because they are very time consuming and expensive to produce. Since machine learning predictions may improve as more data is used to train them, the method was expected to improve with the availability of more time series for training. This improvement was expected to be significant since initially only two time-series (strains) were used for training, out of the three available for each product (the other one was used for testing). Hence, simulated data obtained from using the kinetic model developed for the limonene pathway (FIGS. 4 and 7) was used to determine: (1) how much predictions improve as more time-series data sets are added and (2) how many time series are needed to guide pathway design effectively. A pool of 10,000 sets of time-series data with different protein profiles was created that shared the same kinetic constants. The pool of time-series data was fed the machine learning model in groups of 2, 10, and 100 times series randomly sampled from this pool in order to determine how quickly the model was able to recover the original simulated dynamics. In order to gauge the variability of the predictions (i.e., how predictions change as different training sets are used) as a function of training group size (2, 10, or 100), the predictions were repeated ten times for each training group size.

Figure 12:
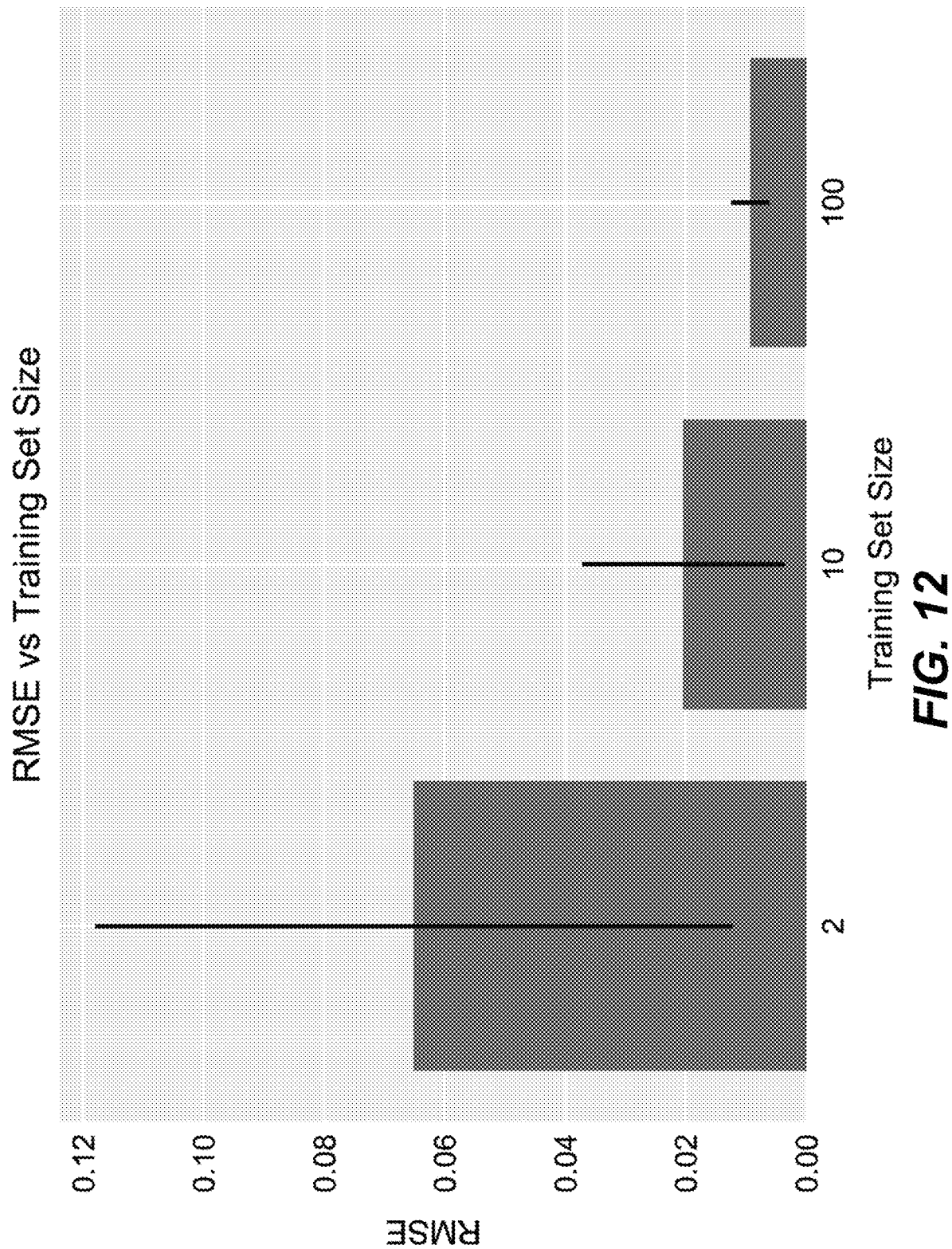
FIG. 12 is a bar chart showing that prediction errors decreased markedly with increasing training set size. As the number of available proteomics and metabolomics times-series data sets (strains) for training increased, the prediction error (RMSE, Eq. (6)) decreased conspicuously. Moreover, the standard deviation of the predictions error (vertical bar) decreased notably as well. The change from 2 to 10 strains was more pronounced that the change from 10 to 100. This observation indicated that it would be more productive to do ten rounds of metabolic engineering collecting ten time-series data sets, than a single round collecting 100 time series.
Figure 13A:
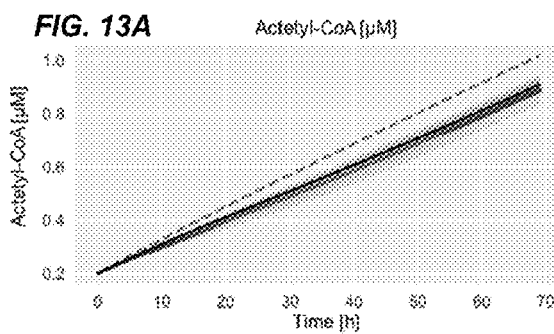
FIGS. 13A-13J show line graphs illustrating that predictions improved with more training data sets. The machine learning process was used to predict kinetic models for varying sizes of training sets (2, 10, and 100 virtual strains in blue, red and black). Ten unique training sets were used for each size to show prediction variability (shown by the shadings) for each training set size. All models converge towards the actual dynamics with the 100 strain models in closest agreement. Standard deviations (shown by the shadings) also decreased markedly as the size of the training set increases.
Figure 13B:
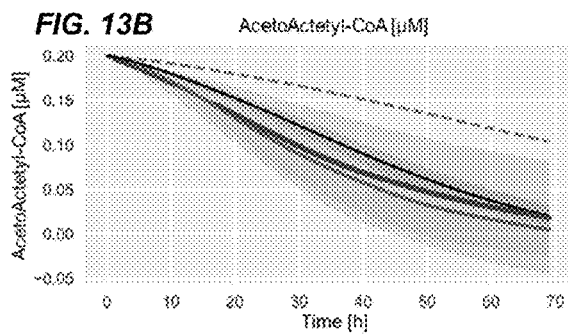
Figure 13C:
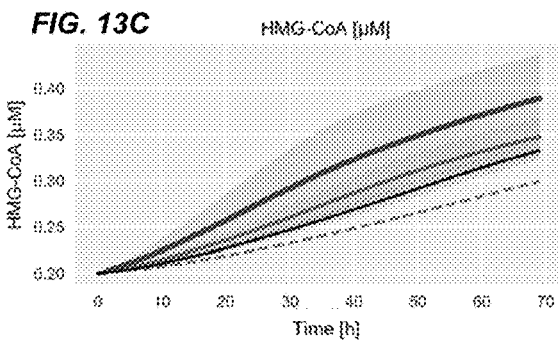
Figure 13D:
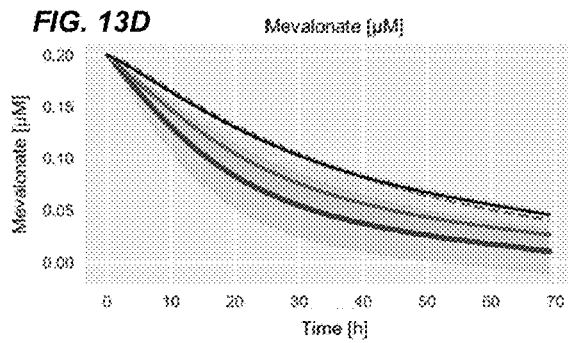
Figure 13E:
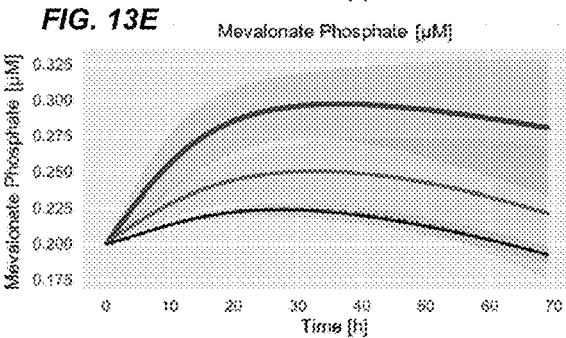
Figure 13F:
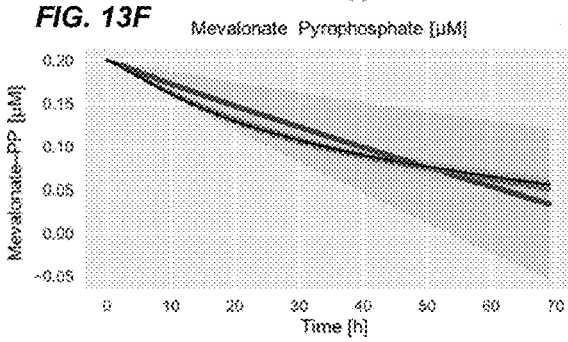
Figure 13G:
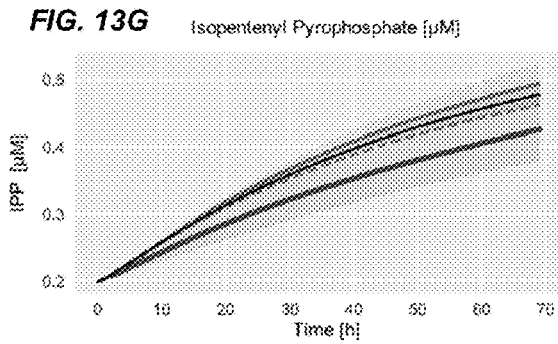
Figure 13H:
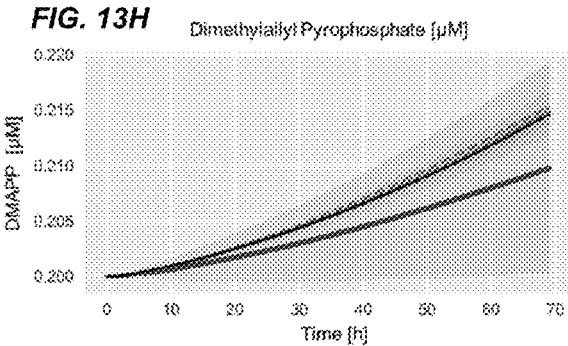
Figure 13I:
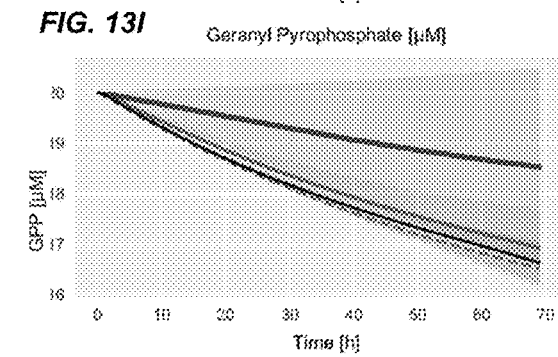
Figure 13J:
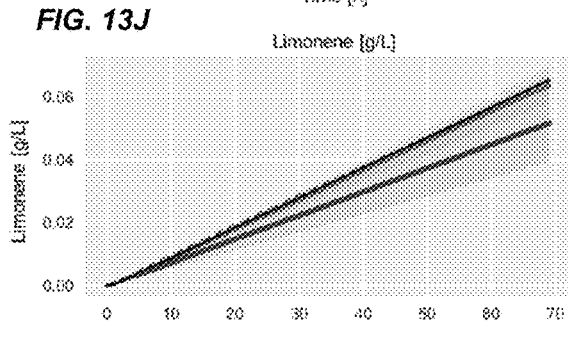

The prediction error (RMSE, Eq. (6)) decreased monotonically as a function of the number of time-series (strains) used to train the model in a nonlinear fashion (FIG. 12). Also, the standard deviation of the predictions significantly decreased with the number of training of data sets (FIGS. 13A-13J). The standard deviation is an indication of the variability of pathway dynamics predictions due to stochastic effects of the optimization processes (e.g., different seeds) and lack of extrapolability from a reduced set of initial protein concentrations. Hence, a predictive model trained with 10 or 100 data sets may produce more robust predictions than a model trained with two data sets. In fact, the high standard deviations observed for models trained on only two data sets may explain the prediction variability observed in the previous section due to stochastic effects. There was a limited drop in error and standard deviation from 10 to 100 strains, with the decrease from two to 10 being the largest (FIG. 12). This may indicate that it is more productive to do ten rounds of engineering collecting ten time-series data set than a single round collecting 100 time series: in this way, ten time series produce accurate enough predictions to pinpoint the desirable part of proteomics of phase space, new strains can be engineered around that space so that new multiomics time series can be obtained around the desirable phase space and optimize for prediction accuracy around that area of phase space. Doing this ten times may be more accurate than a single prediction based on 100 time series that may not be close to the ultimately desirable proteomics phase space. Furthermore, it indicates that the results from the previous section may have been much more reliable if only eight time series more had been available for training.

Accurate Model Predictions for Guiding Pathway Design and Produce Biological Insights The machine learning predictions may not need to be 100% quantitatively correct to accurately predict the relative ranking of production for different strains. Being able to reliably predict which of several possible pathway designs will produce the highest amount of product is very valuable in guiding bioengineering efforts and accelerating them in order to improve titer, rate, and yield (TRY). These process characteristics may be important determinants of economic relevance.

Figure 14A:
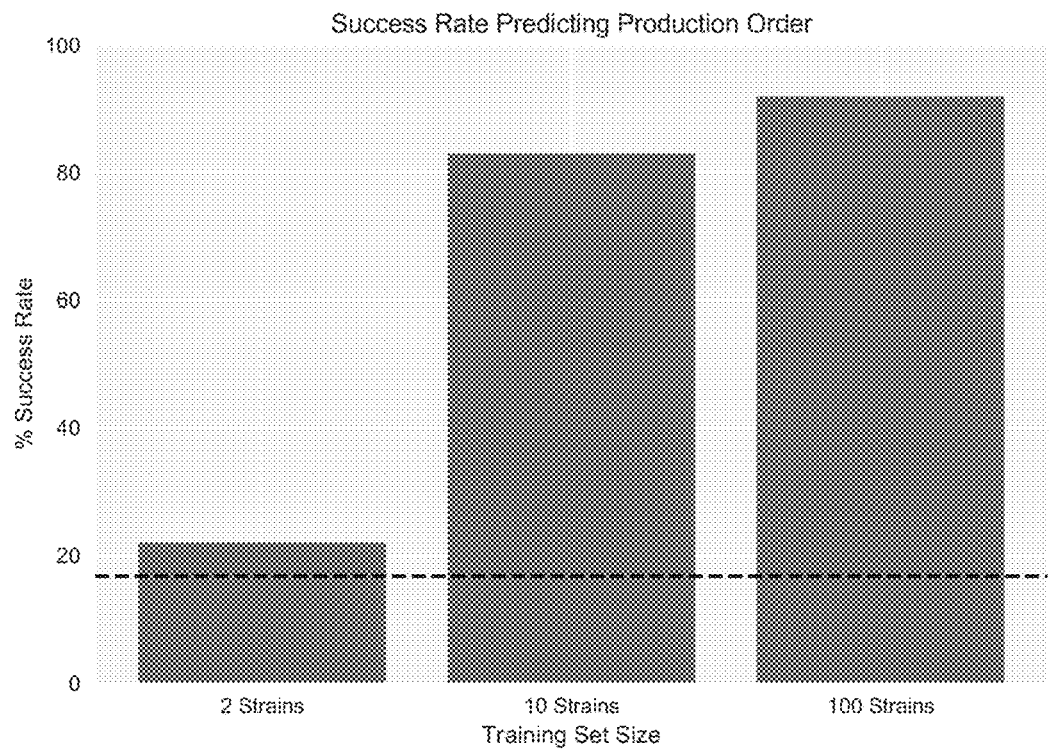
FIGS. 14A and 14B show how the success rate of predicting production ranks increased with training set size.
Figure 14B:
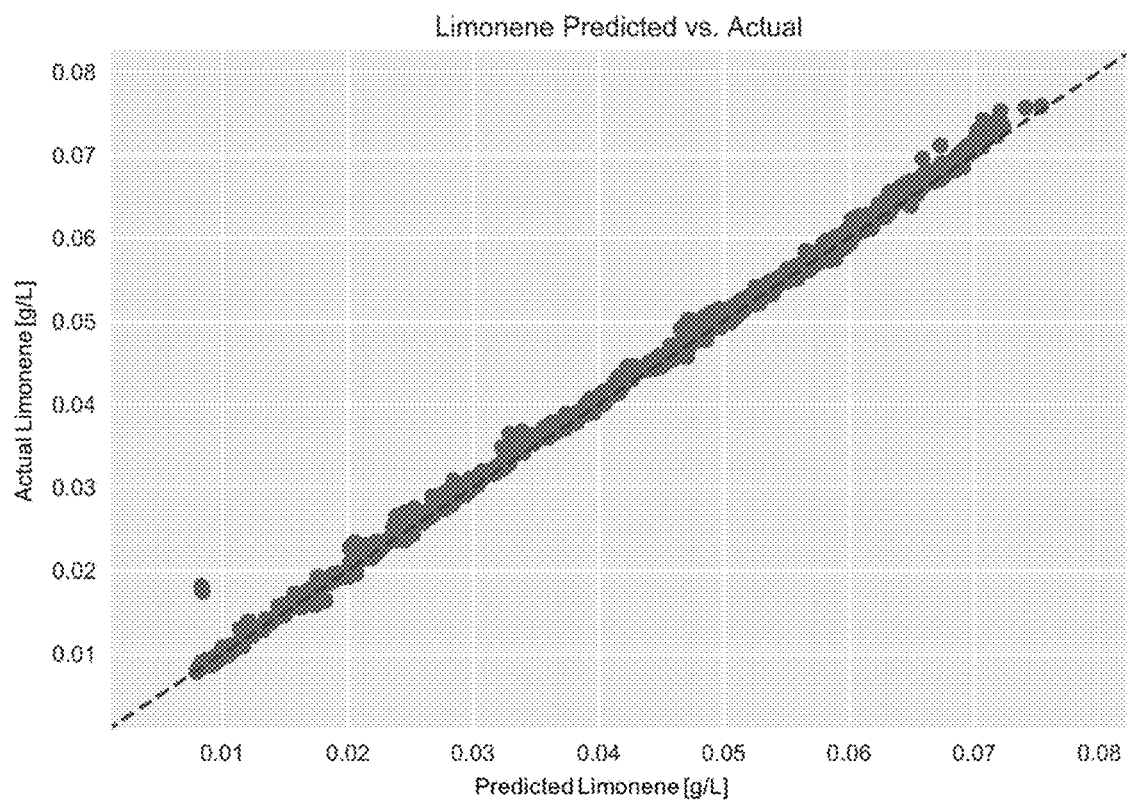

The machine learning model or process was able to reliably predict the relative production ranking for groups of three randomly chosen strains (highest, lowest, and medium producer, mimicking the available experimental data) chosen from the pool of 10,000 time-series data sets mentioned above (FIG. 14A). The success rate depended on the number of data sets available for training: starting at 22% for only two strains up to 92% for 100 training sets. For ten strains the success rate was ~80%, which is reliable enough to practically guide metabolic engineer efforts to improve TRY. For models trained using 100 time series, the prediction errors were minimal (FIG. 14B).

Biological insights may be generated by using the machine learning (ML) model to produce data in substitution of bench experiments. For example, similarly to principal component analysis of proteomics (PCAP), the ML simulations may be used to determine which proteins to over or under express, and for which base strain, in order to improve production (FIGS. 15A and 15B). Proteins LS, AtoB, PMD, and Idi may be important drivers of production in the case of limonene: changing protein expression along the principal component associated with them increases limonene creation (FIG. 15A). Furthermore, this approach provided expected behavior for all metabolites in the pathway, and hypotheses can be made and tested experimentally (FIG. 15B).

To show how biological insights can be derived (FIGS. 15A and 15B), a ML model may be trained using a number of proteomics and metabolomics time series, using the Michaelis-Menten kinetic model as ground truth. For example, the number of proteomics and metabolomics time series may be 50. Additional proteomics time series may be held back as a test data set. For example, the number of metabolite time series used as a test data set may be 50. Each metabolite time series may be predicted using the machine learning model and the associated proteomic time series. The final time point proteomics and final production may be collected for each predicted strain. The final time point proteomics data may be plotted in two dimensions with a basis selected by performing a partial least squares (PLS) regression between the proteomics and final production data. These first basis vector from a PLS regression is the direction that explains the most covariance between the proteomics data and production data. The PLS regression was implemented by and used from scikit-learn.

Data Constraints

Since the ML approach is data-based, data quantity and quality concerns are important. Data quantity concerns involve both the availability of enough time series as well as time points sampled in each time series.

The training set used in this example is one of the largest data sets characterizing a metabolically engineered pathway at regular time intervals through proteomics and metabolomics. There are no larger data sets that include: time series, several types of omics data, more than seven time points, and several strains. For example: the *E. coli* multiomics database has proteomics and metabolomics data for several strains, but no time series. For example, the database may include proteomics and metabolomics data but only one time series with fewer time points (five instead of seven); one time series and only one time point for proteomics; only time-series metabolomics data; metabolomics and proteomics data are not combined; genomics and not have any time-series proteomics or metabolomics; and any or minimal studies in terms of data points and strains.

In order to get enough pairs of derivatives and proteomics and metabolomics data to train ML models (FIG. 3), data augmentation (filtering and interpolation, FIG. 2 and FIG. 5) was used, expanding the initial seven time points to 200 by assuming continuity in the multiomics data (a reasonable assumption). It would be desirable to have more time points available, so as to not to depend on these data augmentation techniques. However, data sets including more time points were nonexistent for physical, biological, and economical reasons. Every time a sample is taken for omics analysis, the volume in the culture flask diminishes and, if the total sampled volume is comparable to the total volume, it may significantly affect the strain physiology. Since taking excessive samples may affect measurements, and these coupled omics analysis are expensive and require specialized personal, the maximum amount of time points was approximately seven. Another reason more time points have not been typically collected is that experts in multiomics data collection consider this sampling rate to fully capture the physiology of strains based on previous experience. The fact that it was possible to produce reasonable predictions for a third time series that the model has never seen before (test strain) validates this.

These results show that a data-centric approach to predicting metabolism that can greatly benefit the biotechnology and synthetic biology industries to enable reliable production. This approach is agnostic as to the pathway, host or product used, and can be systematically applied. This example also shows that, given sufficient data, the dynamics of complex coupled nonlinear systems relevant to metabolic engineering can be systematically learned.

Terminology

In at least some of the previously described embodiments, one or more elements used in an embodiment can interchangeably be used in another embodiment unless such a replacement is not technically feasible. It will be appreciated

TABLE 2

Basis Vectors of Partial Least Squares Regression. The first two components of the partial least squares regression are shown. These components represent the line that explains the most covariance in the dependent variable of final production.

| AtoB | HMGS | HMGR | MK | PMK | PMD | Idi | GPPS | LS |
|---|---|---|---|---|---|---|---|---|
| −0.375 | −0.098 | 0.006 | −0.191 | −0.242 | −0.372 | −0.312 | 0.021 | 0.719 |
| −0.018 | 0.426 | 0.504 | −0.274 | 0.446 | −0.259 | −0.422 | −0.078 | −0.193 | by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for simulating the pathway dynamics of a virtual strain of an organism, comprising:
   computer-readable memory storing executable instructions; and
   one or more hardware processors programmed by the executable instructions to perform a method comprising:
      receiving time-series multiomics data of a plurality of strains of the organism, the times-series multiomics data comprising time-series metabolomics data and time-series proteomics data associated with a metabolic pathway;
      determining derivatives of the time-series metabolomics data;
      training a machine learning model, representing a metabolic pathway dynamics model, using the time-series multiomics data and the derivatives of the time-series metabolomics data, wherein the metabolic pathway dynamics model relates the time-series metabolomics data and time-series proteomics data to the derivatives of the time-series metabolomics data; and
      simulating a virtual strain of the organism using the metabolic pathway dynamics model to determine a characteristics of a metabolic pathway represented by the metabolic pathway dynamics model in the virtual strain.

2. The system of claim 1, wherein the method further comprises:
   designing one or more new strains based on the virtual strain;
   generating experimental time-series multiomics data for the new strains; and
   retraining the machine learning model based on the experimental time-series multiomics data of the new strains.

3. The system of claim 1, wherein the characteristic of the metabolic pathway is a titer, rate, or yield of a product of the metabolic pathway.

4. The system of claim 1, wherein the time-series multiomics data comprises time-series multiomics data of a plurality of strains of an organism.

5. The system of claim 1, wherein the metabolic pathway comprises a heterologous pathway.

6. The system of claim 1, wherein the machine learning model comprises a supervised machine learning model.

7. The system of claim 1, wherein the machine learning model comprises a non-classification model, a neural network, a recurrent neural network (RNN), a linear regression model, a logistic regression model, a decision tree, a support vector machine, a Naïve Bayes network, a k-nearest neighbors (KNN) model, a k-means model, a random forest model, a multilayer perceptron, or a combination thereof.

8. The system of claim 1, wherein the metabolic pathway dynamics model comprises parameters representing kinetics of the metabolic pathway and parameters associated with the plurality of strains.

9. The system of claim 1, wherein training the machine learning model comprises training the machine learning model using training data comprising triplets of a protein concentration, a metabolite concentration, and a metabolite derivative.

10. The system of claim 1, wherein simulating the virtual strain of the organism comprises integrating the metabolic pathway dynamics model over a time period of interest.

11. The system of claim 1, wherein simulating the virtual strain of the organism comprises determining a concentration of a metabolite of the metabolic pathway using the metabolic pathway dynamics model.

12. The system of claim 1, wherein the one or more hardware processor is further programmed to: smooth the time-series metabolomics data to generate smoothed time-series metabolomics data, wherein determining the derivatives of the time-series metabolomics data comprises determining derivatives of the smoothed time-series metabolomics data, and wherein training the machine learning model comprises training the machine learning model using the smooth time-series multiomics data and the derivatives of the smoothed metabolomics data.

13. The system of claim 11, wherein smoothing the time-series metabolomics data comprises smoothing the time-series metabolomics data using a filter.

14. The system of claim 11, wherein the filter comprises a Savitzky-Golay filter.

15. A method for simulating the metabolic pathway dynamics of a strain of an organism, comprising:
receiving time-series multiomics data comprising a first time-series multiomics data associated a metabolic pathway and a second time-series multiomics data associated with the metabolic pathway;
determining derivatives of the first time-series multiomics data;
training a machine learning model, representing a metabolic pathway dynamics model, using the first time-series multiomics data, the derivatives of the first time-series multiomics data, and the second time-series multiomics data, wherein the metabolic pathway dynamics model relates the first time-series multiomics data and the second time-series multiomics data to the derivatives of the first time-series multiomics data; and
simulating a virtual strain of the organism using the metabolic pathway dynamics model.

16. The method of claim 15, wherein the first time-series multiomics data comprises time-series metabolomics data of a plurality of strains of an organism, wherein the time-series metabolomics data comprises two or more time-series of a strain.

17. The method of claim 15, wherein the second time-series multiomics data comprises time-series proteomics data of a plurality of strains of an organism, and wherein the time-series proteomics data comprises a plurality of time-series of a strain.

18. The method of claim 15, wherein the first time-series multiomics data comprises time-series multiomics data of a plurality of strains of an organism, and wherein the first time-series multiomics data comprises time-series multiomics data of a plurality of strains of a different organism.

19. The method of claim 15, wherein the first time-series multiomics data or the second time-series multiomics data comprises time-series proteomics data, time-series metabolomics data, time-series transcriptomics data, or a combination thereof.

20. The method of claim 15, wherein the first time-series multiomics data or the second time-series multiomics data is associated with an enzymatic characteristic selected from the group consisting of a $k_{cat}$ constant, a $K_m$ constant, and a kinetic characteristics curve.

21. The method of claim 15, wherein the first time-series multiomics data and the second time-series multiomics data comprise observations at corresponding time points.

22. The method of claim 15, wherein the machine learning model comprises a supervised machine learning model.

23. The method of claim 15, wherein the metabolic pathway dynamics model comprises observable and unobservable parameters representing kinetics of the metabolic pathway.

24. The method of claim 15, wherein training the machine learning model comprises training the machine learning model using training data comprising an n-tuples of a first observation at a time point in the first time-series multiomics data, a second observation at the time point in the second time-series multiomics data, and a derivative of the first observation.

25. The method of claim 15, wherein training the machine learning model comprises selecting the machine learning model from a plurality of machine learning models using a tree-based pipeline optimization tool.

26. The method of claim 15, wherein simulating the virtual strain of the organism comprises integrating derivatives of the first time-series multiomics data outputted by the metabolic pathway dynamics model.

27. The method of claim 15, wherein simulating a virtual strain of the organism using the metabolic pathway dynamics model comprises simulating a virtual strain using the metabolic pathway dynamics model to change one or more of titer, rate, and yield of a product of a metabolic pathway represented by the metabolic pathway dynamics.

28. The method of claim 15, further comprising designing a strain of the organism corresponding to the simulated strain.

29. The method of claim 15, further comprising creating a strain of the organism corresponding to the simulated strain.

* * * * *